United States Patent
Pinsonneault et al.

(10) Patent No.: US 10,742,654 B1
(45) Date of Patent: Aug. 11, 2020

(54) PRESCRIPTION PRIOR AUTHORIZATION SYSTEM

(71) Applicant: McKesson Corporation, Irving, TX (US)

(72) Inventors: Roger G. Pinsonneault, Alpharetta, GA (US); Elizabeth S. Kaye, Suwanee, GA (US)

(73) Assignee: McKesson Corporation, Irving, TX (US)

( * ) Notice: Subject to any disclaimer, the term of this patent is extended or adjusted under 35 U.S.C. 154(b) by 473 days.

(21) Appl. No.: 15/086,818

(22) Filed: Mar. 31, 2016

(51) Int. Cl.
| | |
|---|---|
| *G16H 20/10* | (2018.01) |
| *H04L 29/06* | (2006.01) |
| *G06F 19/00* | (2018.01) |
| G16H 20/90 | (2018.01) |
| G16H 20/60 | (2018.01) |
| G16H 20/70 | (2018.01) |

(52) U.S. Cl.
CPC .......... *H04L 63/10* (2013.01); *G06F 19/3456* (2013.01); *G16H 20/10* (2018.01); *G16H 20/60* (2018.01); *G16H 20/70* (2018.01); *G16H 20/90* (2018.01)

(58) Field of Classification Search
CPC ..... H04L 63/10; G06F 19/3456; G16H 20/10; G16H 20/60; G16H 20/70; G16H 20/90
USPC .......................................................... 705/2
See application file for complete search history.

(56) References Cited

U.S. PATENT DOCUMENTS

| | | | | |
|---|---|---|---|---|
| 5,608,874 A | * | 3/1997 | Ogawa ............... | H04N 1/00204 709/246 |
| 8,392,214 B1 | * | 3/2013 | Pinsonneault ......... | G06Q 50/22 235/378 |
| 9,361,464 B2 | | 6/2016 | Wu | |
| 2014/0222464 A1 | * | 8/2014 | Sharaf ................... | G06F 19/328 705/3 |
| 2015/0278472 A1 | * | 10/2015 | King ................... | G06F 19/3456 705/2 |
| 2015/0324547 A1 | * | 11/2015 | Graham .............. | G06F 19/3456 705/2 |

* cited by examiner

*Primary Examiner* — Robert A Sorey
*Assistant Examiner* — Kimberly A. Sass
(74) *Attorney, Agent, or Firm* — Alston & Bird LLP

(57) ABSTRACT

An improved prescription prior authorization system is disclosed and described herein. The improved prescription prior authorization system provides an improved system and apparatus for prescription prescribers and other healthcare providers to satisfy prior authorization requirements as part of the prescription process. The improved prescription prior authorization system provides mechanisms to a prescriber of medication to more quickly and efficiently satisfy prior authorization requirements for a prescriber and to more quickly provide the prescription to the patient to improve the patient's overall health. The patient's overall health is improved because of the improved likelihood that the patient will receive the product that the prescriber wants to prescribe to the patient. The improved prescription prior authorization system also reduces prescription network traffic and improves the efficiency of the prescription network.

16 Claims, 7 Drawing Sheets

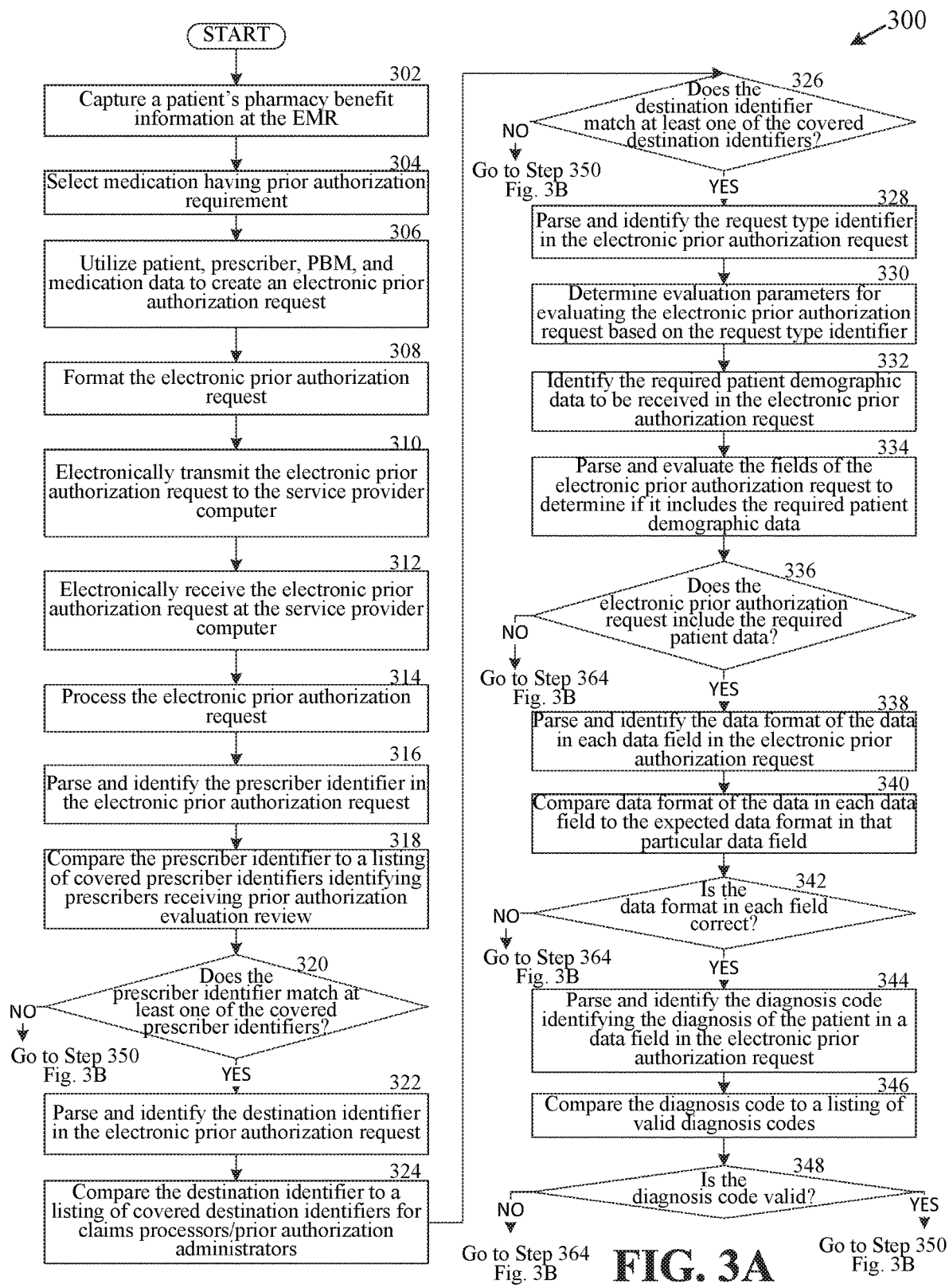

PRESCRIPTION PRIOR AUTHORIZATION SYSTEM

TECHNICAL FIELD

Aspects of the disclosure relate generally to prior authorizations systems, and more particularly, to an improved prescription prior authorization system.

BACKGROUND

A healthcare provider that is legally permitted to prescribe medications, products, and/or services to a patient (herein referred to as a prescriber) may often have many options to choose from when selecting a prescription regimen for a patient. In many cases it is important to the overall health of the patient that the patient fill this prescription and follow the prescriber's prescription regimen. One problem that can occur is that the prescriber may write a prescription for a particular medication, product, or service and when the patient tries to fill the prescription, the patient may be informed that their pharmacy benefits provider will not cover any portion of the cost of the prescribed medication, product, or service because a prior authorization to obtain the prescribed medication, product, or service was necessary before the medication, product, or service could be prescribed. While prior authorization can be obtained from the pharmacy benefits provider after the medication has been prescribed, it can take several days to occur. This can result in the patient not filling the prescription and potentially not informing the prescriber that the prescription was never filled and the patient is not following the prescription regimen. In addition, the requirements for requesting prior authorization can be very detailed and elaborate. Errors in requests for prior authorization can further slow the process of obtaining prior authorization from the pharmacy benefits provider. Correcting those errors that are correctable in line with the processing of prior authorization requests can speed up the overall processing of prior authorization requests and improve the likelihood that the patient follows the prescription regimen.

BRIEF DESCRIPTION OF THE DRAWINGS

Reference will now be made to the accompanying drawings, which are not necessarily drawn to scale, and wherein:

FIGS. 3A-B are an example methodology for an improved prescription prior authorization system, in accordance with one exemplary embodiment.

DETAILED DESCRIPTION OF EXEMPLARY EMBODIMENTS

Figure 1:
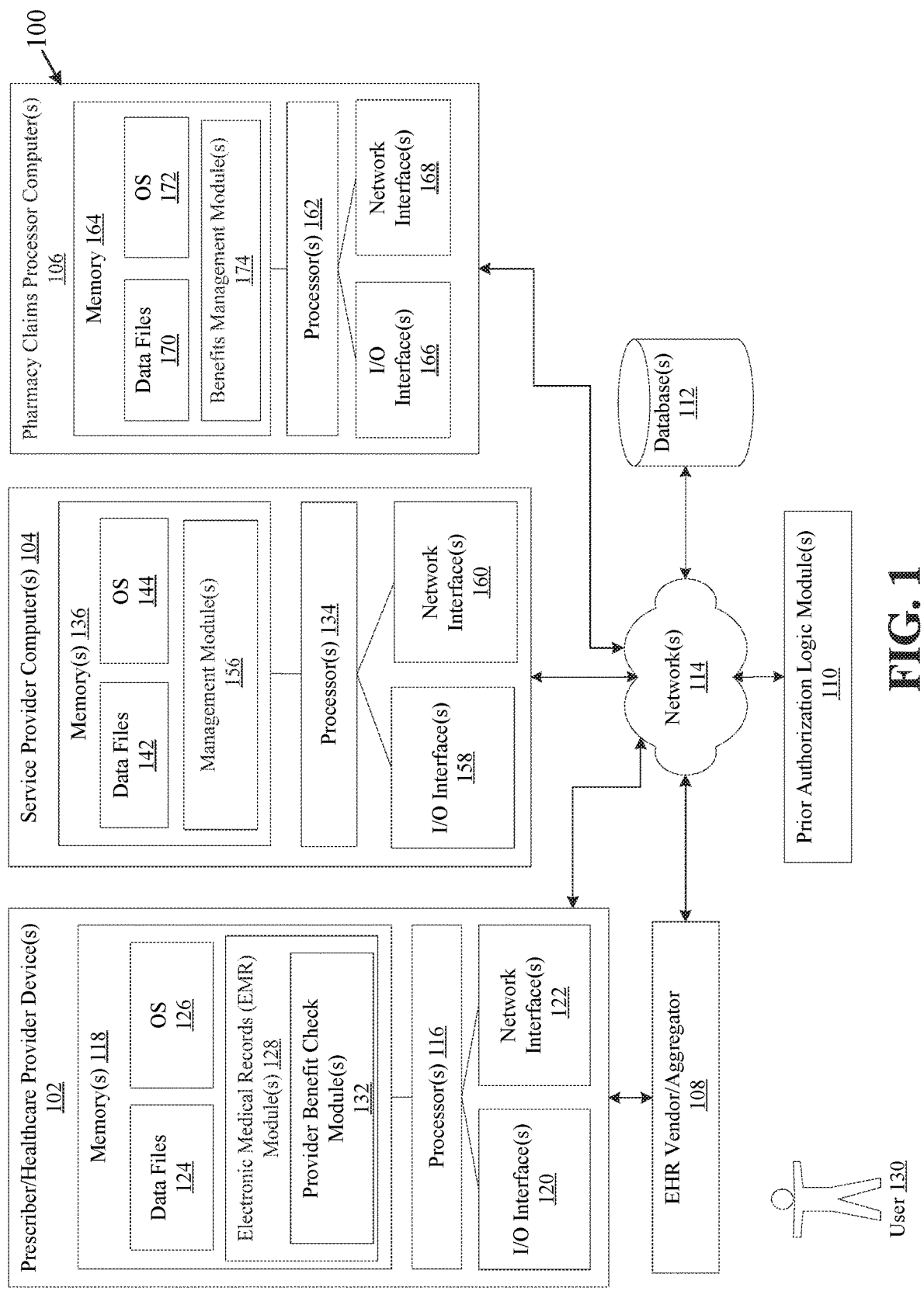
FIG. 1 illustrates an example overview of a system that facilitates the improved provision of prior authorization services according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include systems and methods that facilitate the improved provision of prescription prior authorization services to prescribers of medication and patients as part of or in-line with the processing of one or more types of electronic prior authorization requests, such as an electronic prior authorization initiation request, an electronic prior authorization request, an electronic prior authorization appeal request, or an electronic prior authorization cancel request formatted under the National Council for Prescription Drug Programs (NCPDP) Script Standard, in real-time or near real-time. For example, a prescriber of a medication, product, or service may access a patient's medical records via an electronic medical records (EMR) system and generate an electronic prior authorization request. The prescriber may electronically transmit the electronic prior authorization request to a service provider computer either directly or indirectly via an electronic healthcare records (EHR) vendor/aggregator system over a network. In one example, each EHR vendor/aggregator system can be a vendor of EHR programs and systems provided to multiple healthcare providers and/or an aggregator of EHR data from the multiple healthcare providers and can act as a conduit for electronic requests and/or responses electronically communicated between the healthcare provider device and the service provider computer via the network.

The service provider computer may electronically receive the electronic prior authorization request and may evaluate one or more data fields in the electronic prior authorization request to determine if the electronic prior authorization request includes at least the minimum data required for submission of the request and/or if each data field of the request includes data in a proper format. If the service provider computer determines that the minimum data required is not provided in the electronic prior authorization request and/or the format of data in one or more data fields is incorrect, the service provider computer can generate an electronic prior authorization response that includes a denial of the electronic prior authorization request and a message describing the reason for the denial. The service provider computer can then electronically transmit the electronic prior authorization response to the healthcare provider device for the prescriber (either directly or indirectly via the EHR vendor/aggregator system) via the network.

In addition, or in the alternative, the service provider computer can evaluate one or more data fields of the electronic prior authorization request to determine if the data in those fields is in the correct format. If the data in one or more data fields is not in the correct format, the service provider computer can identify the data in the correct data format and modify the electronic prior authorization request by removing the data in the incorrect format and replacing it with the data in the correct format. The service provider computer can also electronically transmit the electronic prior authorization request to a claims processor computer or prior authorization clearinghouse via the network for processing.

In addition, the service provider computer can receive an electronic prior authorization response via the network from the claims processor computer or the prior authorization clearinghouse. The service provider computer can evaluate the request or response to identify the medication identifier and determine if there are any financial assistance programs or other forms of patient messaging associated with the medication identifier. The service provider can insert notifications of the financial assistance programs or other patient messaging into the electronic prior authorization response or can append those messages to the response and can electronically transmit the electronic prior authorization response and messaging to the prescriber at the healthcare provider device either directly or through the EHR vendor/aggregator system and the network.

System Overview

FIG. 1 illustrates an example system 100 supporting the improved provision of prescription prior authorization services to prescribers and patients, according to one example embodiment. As shown in FIG. 1, the system 100 may include one or more prescriber and/or healthcare system devices 102, service provider computers 104, pharmacy claims processor computers 106, and/or EHR vendor/aggregator systems 108. As desired, each of the prescriber and/or healthcare provider devices 102, service provider computer 104, pharmacy claims processor computers 106, and/or EHR vendor/aggregator systems 108 may include one or more processing devices that may be configured for accessing and reading associated computer-readable media having stored data thereon and/or computer-executable instructions for implementing various embodiments of the disclosure.

Additionally, in certain example embodiments, the service provider computer 106 and/or the prior authorization logic module 110 may be in communication with one or more data storage devices, such as database 112. The database 112 may receive, store, and provide, as needed, healthcare requests data from the service provider computer 104 and/or the prior authorization logic module 110. In certain example embodiments, the healthcare requests data includes all or any portion of the data included in electronic prior authorization requests received by the service provider computer 104 from a prescriber/healthcare provider computer 102 (either directly or via an EHR vendor/aggregator system 108) and/or electronic prior authorization responses to the electronic prior authorization requests received from a pharmacy claims processor computer 106 or prior authorization clearinghouse. In addition, the database 112 or another database may include business rules providing methodologies for comparing and evaluating electronic prior authorization requests and associated responses by the service provider computer 104 or the prior authorization logic module 110. The database 112 can also include a schedule table or listing of records for prescribers, vendors, aggregators, claims processors, and/or prior authorization clearinghouses that receive the prior authorization evaluation services. In addition, the database 112 can include a table, schedule, or listing of records for medications that have financial assistance programs and/or those medications that may include additional messaging for the patient (e.g. REMS program messaging or other patient or medication specific messaging) and the associated messaging to be included in the electronic prior authorization response. The database 112 can also include a listing of minimum data requirements for processing each form of electronic prior authorization request, a listing of one or more data fields for each form of electronic prior authorization request and the associated expected data format for data in each of those data fields, and one or more conversion tables for converting data that is in an incorrect format into a correct format. The database can also include patient information (e.g., patient identifiers (e.g., patient social security number, a subset of the patient social security number, health insurance claim number (HICN), cardholder ID, etc.), patient name, patient gender, patient date of birth, patient address, patient zip code), benefits provider identifiers (e.g., Banking Identification Number (BIN Number), BIN Number and Processor Control Number (PCN), or BIN Number and Group ID), benefits provider name, date of service, software and/or vendor certification identification, pharmacy identification qualifier, pharmacy identification (e.g., National Provider Identifier (NPI) code, Drug Enforcement Administration (DEA) number, state license number, NCPDP Provider ID, store and/or chain name, store address, or the like), product/service information (identifier) (e.g., medication/product/service name(s), National Drug Code (NDC) code, RxNorm medication identifiers, days' supply, quantity dispensed, and the like), patient history information including, but not limited to, medication history information (e.g., total number of medications/products/services, medication/product/service name(s), NDC codes, RxNorm medication identifiers, quantity of medication to be dispensed), prescriber identification number (i.e., prescriber ID ((e.g., NPI code, DEA number), prescriber name, and prescriber zip code or other postal zone identifier for a prescription. Alternatively, the data storage function may be included in the service provider computer 104 and/or the prior authorization logic module 110 itself, such as in the memory 136 of the service provider computer 104.

Generally, the service provider computer 104 is a special purpose machine (a switch/router) configured for receiving electronic healthcare requests (including electronic prior authorization requests) from prescriber/healthcare provider computers 102 associated with (e.g., located within or otherwise under the control and administration of) prescribers of medication (e.g., physicians, dentists, nurse practitioners, hospitals, physicians offices, clinics, or any other person or entity legally authorized to prescribe medications, products, or services to patients) either directly or via an EHR vendor/aggregator system 108, and pharmacy computers associated with (e.g., located within or otherwise under the control and administration of) pharmacies, conducting edit or analysis actions on the electronic prior authorization requests, and, in some situations, forwarding the electronic prior authorization requests to a pharmacy claims processor computer associated with (e.g., located within or otherwise under the control and administration of) a pharmacy claims processor or benefits provider (e.g., pharmacy benefits manager (PBM), insurance provider, government insurance provider (e.g., Medicare, Medicaid) or a prior authorization clearinghouse. Further the special purpose service provider computer 106 can be configured to electronically receive electronic prior authorization responses from the pharmacy claims processor computers 108 and/or prior authorization clearinghouses, conduct editing or analysis actions on the electronic prior authorization responses, and forward all or a portion of the data from the electronic prior authorization response and/or modifying or generating new electronic prior authorization responses and forwarding them electronically to the originating prescriber/healthcare provider computer 102 (either directly or via an EHR vendor/aggregator system 108). The special purpose service provider computer 104 can include or otherwise be associated with suitable hardware and/or software for electronically transmitting and receiving data and/or computer-executable instructions over one or more communications links or networks. The special purpose service provider computer 104 may also include any number of processors for processing data and executing computer-executable instructions. Further, the special purpose service provider computer 104 may include or be in communication with any number of suitable memory devices operable to store data and/or computer-executable instructions. By executing computer-executable instructions, the service provider computer 104 forms a special purpose computer or particular machine used for a particular purpose. As used herein, the term "computer-readable medium" describes any form of suitable memory or memory device.

Additionally, in one or more example embodiments of the disclosure, the special purpose service provider computer 104 may include or otherwise be in communication with a prior authorization logic module 110 or prior authorization logic application. The prior authorization logic module 110 may include computer-executable instructions operable for evaluating an electronic prior authorization request and or electronic prior authorization response based at least in part on the parameters and business rules provided in the database or other memory and as described herein.

In addition to receiving and storing information and evaluating electronic prior authorization requests and/or electronic prior authorization responses, the prior authorization logic module 110 may be further operable to access and/or be in communication with one or more suitable databases and/or data storage devices 112. In one example, the prior authorization logic module 110 may also access the data in the database to determine if an electronic prior authorization request should be denied or modified and/or to determine if an electronic prior authorization response should be modified or if additional messaging should be provided along with the response.

The example prescriber or healthcare provider device 102 is not intended to be limited to physician offices alone and may otherwise be associated with any healthcare provider, such as, for example, a prescriber (such as a hospital, urgent care center, clinic, dentist, or any other person legally permitted to prescribe healthcare related products and/or services to patients). While the example prescriber/healthcare provider device 102 is described as being located within a physician's office, this is for example only and is not intended to be limiting in any manner.

Generally, network devices and systems, including one or more prescriber and/or healthcare provider devices 102, pharmacy claims processor computers 106, and/or EHR vendor/aggregator systems 108 may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more prescriber and/or healthcare provider devices 102, service provider computers 104, pharmacy claims processor computers 106, and/or EHR vendor/aggregator systems 108 may be in communication with each other via one or more networks, such as network 114, which may include one or more independent and/or shared private and/or public networks including the Internet or a publicly switched telephone network. In other example embodiments, one or more components of the system 100 may communicate via direct connections and/or communication links. Each of these components—the prescriber and/or healthcare provider device, service provider computer 104, pharmacy claims processor computer 106, EHR vendor/aggregator system 108, and the network 114—will now be discussed in further detail. Although the components are generally discussed as singular components, as may be implemented in various example embodiments, in alternative exemplary embodiments each component may include any number of suitable computers and/or other components.

With continued reference to FIG. 1, one or more prescriber and/or healthcare provider devices 102 may be associated with a prescriber of medication (e.g., physicians, dentists, nurse practitioners, hospitals, physicians offices, clinics, or any other person or entity legally authorized to prescribe medications, products, or services to patients) and/or healthcare provider, for example, a physician, a nurse, a nurse practitioner, a physician's assistant, a hospital, a physician's office, a clinic, a dentist, etc. A prescriber and/or healthcare provider device 102 may be any suitable processor-driven device that facilitates the processing of electronic prior authorization requests (e.g., an electronic prior authorization initiation request, an electronic prior authorization request, an electronic prior authorization appeal request, and/or an electronic prior authorization cancel request formatted under the NCPDP Script Standard) made by or on behalf of, for example, a physician's office for a patient prescription, the communication (either directly or indirectly via the EHR vendor/aggregator system 108) of electronic prior authorization requests to the service provider computer 104, and/or the receipt, processing, and display of electronic prior authorization responses (e.g., electronic prior authorization initiation response, electronic prior authorization response, electronic prior authorization appeal response, and electronic prior authorization cancel response formatted under the NCPDP Script Standard) received (either directly or indirectly via the EHR vendor/aggregator system 108) from the service provider computer 104. For example, the prescriber and/or healthcare provider device 102 may be a computing device that includes any number of server computers, mainframe computers, networked computers, desktop computers, personal computers, mobile devices, smartphones, digital assistants, personal digital assistants, tablet devices, Internet appliances, application-specific integrated circuits, microcontrollers, minicomputers, and/or any other processor-based devices. The prescriber/healthcare provider device 102 having computer-executable instructions stored thereon may form a special-purpose computer or other particular machine that is operable to facilitate the processing of electronic requests for healthcare information made by or on behalf of a prescriber and/or healthcare provider and the electronic transmittal of requested healthcare information, electronic prior authorization requests, and other electronic healthcare requests to the service provider computer 104. Additionally, in certain example embodiments, the operations and/or control of the prescriber/healthcare provider device 102 may be distributed among several processing components. In addition to including one or more processors 116, the prescriber/healthcare provider device 102 may further include one or more memory devices (or memory) 118, one or more input/output ("I/O") interfaces 120, and one or more network interfaces 122. The memory devices 116 may be any suitable memory devices, for example, caches, read-only memory devices, random access memory devices, magnetic storage devices, removable storage devices, etc. The memory devices 118 may store data, executable instructions, and/or various program modules utilized by the prescriber/healthcare provider device 102, for example, data files 124, an operating system ("OS") 126, and/or an electronic medical records (EMR) module 128.

The OS 126 may be a suitable software module that controls the general operation of the prescriber/healthcare provider device 102. The OS 126 may also facilitate the execution of other software modules by the one or more processors 116, for example, the EMR module 128. The OS 126 may be any operating system known in the art or which may be developed in the future including, but not limited to, Microsoft Windows®, Apple OSX™, Apple iOS™ Google Android™, Linux, Unix, or a mainframe operating system.

The electronic medical records (EMR) module 128 may be a software application, including, but not limited to, a dedicated program: for making diagnoses; for determining prescriptions, over-the-counter medications, products, or other healthcare services associated with one or more diagnoses; for creating prescription benefit check requests, and for creating electronic prior authorization requests; for reading and/or updating medical records, as well as interacting with the service provider computer 104 either directly or indirectly via the EHR vendor/aggregator system 108. For example, a user 130, such as a prescriber or other healthcare system employee, may utilize the EMR module 128 of the prescriber/healthcare provider device 102 during a patient visit, for optionally capturing the patient's pharmacy benefit information. Furthermore, the prescriber/healthcare provider device 102 may utilize the EMR module 128 to retrieve or otherwise receive data, messages, or responses (either directly or indirectly via the EHR vendor/aggregator system 108) from the service provider computer 104 and/or other components of the system 100.

The EMR module 128 may also engage the provider benefit check module 132 to communicate electronic prior authorization requests (either directly or indirectly via the EHR vendor/aggregator system 108) to the service provider computer 104 for use in determining whether the patient's benefits provider (e.g., via the pharmacy claims processor computer 106 or associated with the patient's benefits provider) or prior authorization clearinghouse will approve the electronic prior authorization request and display the electronic prior authorization response and potentially additional patient or medication related messaging information to the prescriber for communication to the patient. The provider benefit check module 132 may gather all the required and available optional data including, but not limited to, the medication/product/service information (e.g., total number of medications, medication name(s), NDC code(s), RxNorm medication identifiers, medication or product quantity to be dispensed to the patient, days' supply, etc.), patient information (e.g., patient name, patient gender, patient date of birth, patient zip or other postal zone identifier), and prescriber identification number (i.e., prescriber ID ((e.g., NPI code, DEA number)), prescriber name, and prescriber ZIP code or other postal zone identifier. Following the information collection, the provider benefit check module 132 formats one or more electronic prior authorization requests (e.g., an electronic prior authorization initiation request, an electronic prior authorization request, an electronic prior authorization appeal request, or an electronic prior authorization cancel request) for a patient prescription according to NCPDP Script Standards in the agreed upon format. The electronic prior authorization request may then be electronically transmitted (either directly or indirectly via the EHR vendor/aggregator system 108) to the service provider computer 104 via the network 114.

The one or more I/O interfaces 120 may facilitate communication between the prescriber/healthcare provider device 102 and one or more input/output devices, for example, one or more user interface devices, such as a display, keypad, control panel, touch screen display, remote control, mouse, microphone, etc., that facilitate user interaction with the prescriber/healthcare provider device 102. For example, the one or more I/O interfaces 120 may facilitate entry of information associated with an electronic prior authorization requests by a prescriber or other healthcare provider, such as a physician. The one or more network interfaces 122 may facilitate connection (either directly or indirectly via the EHR vendor/aggregator system 108) of the prescriber/healthcare provider device 102 to one or more suitable networks, for example, the network 114 illustrated in FIG. 1. In this regard, the prescriber/healthcare provider device 102 may electronically receive and/or transmit (either directly or indirectly via the EHR vendor/aggregator system 108) information to other network components of the system 100, such as the service provider computer 104.

With continued reference to FIG. 1, one or more special-purpose service provider computers 104 may be associated with (e.g., located at or under the control of) a service provider. The service provider computer 104 is a processor-driven device that is configured for electronically receiving, processing, and fulfilling requests from the one or more prescriber/healthcare provider computers 102, one or more pharmacy computers, the one or more pharmacy claims processor computers 106, the network benefit check module 110, and/or the one or more databases 112, relating to pharmacy, benefits, billing, electronic prescription delivery and submission, and/or other healthcare requests and/or other activities. The service provider computer 104 is a special purpose switch/router device that electronically routes electronic prior authorization requests, from a prescriber/healthcare provider computer 102 (either directly or via the EHR vendor/aggregator system 108) to a pharmacy claims processor computer 106.

The service provider computer 104 may include any number of special-purpose computers or other particular machines, application-specific integrated circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors associated with the service provider computer 104 to form a special-purpose computer or other particular machine that is operable to facilitate the receipt, routing, and/or processing of electronic prior authorization requests. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

The service provider computer 104 may include one or more processors 134, one or more memory devices 136, one or more input/output ("I/O") interfaces 138, and one or more network interfaces 140. The one or more memory devices 136 may be any suitable memory device, for example, caches, read-only memory devices, etc. The one or more memory devices 136 may store data, executable instructions, and/or various program modules utilized by the service provider computer 104, for example, data files 140 and an operating system ("OS") 144. The OS 144 may be any operating system known in the art or which may be developed in the future including, but not limited to, Microsoft Windows®, Apple OSX™, Linux, Unix, Apple iOS™, Google Android™, or a mainframe operating system. The OS 144 may be a suitable software module that controls the general operation of the service provider computer 104 and/or that facilitates the execution of other software modules.

According to an example embodiment, the data files 142 may store healthcare request records associated with communications received from various prescriber/healthcare provider devices 102 (either directly or via the EHR vendor/aggregator system 108) and/or various pharmacy claims processor computers 106. The data files 142 may also store any number of suitable routing tables that facilitate determining the destination of communications received from a prescriber/healthcare provider device 102 and/or a pharmacy claims processor computer 106. In one or more example embodiments, the service provider computer 104 may include or otherwise be in communication with one or more suitable databases and/or data storage devices 112.

The service provider computer 104 may include additional program modules for performing other processing methods described herein. Those of ordinary skill in the art will appreciate that the service provider computer 104 may include alternate and/or additional components, hardware, or software without departing from the scope of the disclosure. The management module 156 may be an Internet browser or other software, such as a dedicated program, for interacting with the prescriber/healthcare provider device 102 (either directly or via the EHR vendor/aggregator system 108), and/or the pharmacy claims processor computers 106. Alternatively, the management module 156 may also be implemented as computer-implemented instructions of a memory of a separate computing entity or processor-based system, according to another example embodiment of the disclosure.

With continued reference to the service provider computer 104, the one or more I/O interfaces 158 may facilitate communication between the service provider computer 104 and one or more input/output devices, for example, one or more user interface devices, such as a display, keypad, mouse, control panel, touch screen display, remote control, microphone, etc., that facilitate user interaction with the service provider computer 104. The one or more network interfaces 160 may facilitate connection of the service provider computer 104 to one or more suitable networks, for example, the network 114 illustrated in FIG. 1. In this regard, the service provider computer 104 may communicate with other components of the system 100.

With continued reference to FIG. 1, any number of pharmacy claims processor computers or prior authorization clearinghouses 106 (referred to hereinafter as "pharmacy claims processor computer(s) 106") may be associated with any number of pharmacy claims processors (e.g., pharmacy benefits manager (PBM), insurance provider, government insurance provider (e.g., Medicare, Medicaid) or a prior authorization clearinghouse. Each pharmacy claims processor computer 106 may be any suitable processor-driven devices, such as, but not limited to, a server computer, a personal computer, a laptop computer, a handheld computer, and the like. In addition to having one or more processors 162, the pharmacy claims processor computer 106 may further include one or more memories 164, one or more input/output (I/O) interfaces 166, and one or more network interfaces 168. The memory 164 may store data files 170 and various program modules, such as an operating system (OS) 172 and a benefits management module 174. The I/O interface(s) 166 may facilitate communication between the processors 162 and various I/O devices, such as a keyboard, mouse, printer, microphone, speaker, monitor, bar code reader/scanner, RFID reader, and the like. The network interface(s) 170 each may take any of a number of forms, such as a network interface card, a modem, a wireless network card, and the like.

Generally, the pharmacy claims processor computer 106 may facilitate the determination/processing of electronic prior authorization requests (e.g., an electronic prior authorization initiation request, an electronic prior authorization request, an electronic prior authorization appeal request, and/or an electronic prior authorization cancel request formatted according to the NCPDP Script Standard). According to various example embodiments, the pharmacy claims processor computer 106 may be associated with, without limitation, a PBM, an insurance company, a government healthcare provider, another third-party payor, a prior authorization clearinghouse, or a pharmacy claims processor processing electronic prior authorization requests on behalf of one or more third-party payors and/or healthcare providers.

The pharmacy claims processor computer 106 may include the benefits management module 174. The benefits management module 174 may be an Internet browser or other software, such as a dedicated program, for interacting with the service provider computer 104. The benefits management module 174 may be operable to access one or more databases in database 112 or in another database communicably coupled to the pharmacy claims processor computer 106. In one example, the pharmacy claims processor computer 106 may have a dedicated connection to the database 112. However, the pharmacy claims processor computer 106 may also communicate with the database 112 via the network 114 shown, or via another network.

With continued reference to FIG. 1, the system 100 may include any number of EHR vendor/aggregator systems 108. Each EHR vendor/aggregator system 108 may be associated with any number of prescriber/healthcare provider devices and computer systems 102. For example, each EHR vendor/aggregator system 108 can be a vendor of EHR programs and systems provided to multiple prescribers/healthcare providers and/or an aggregator of EHR data from the multiple prescribers/healthcare providers and can act as a conduit for electronic requests and/or responses electronically communicated between the prescriber/healthcare provider device 102 and the service provider computer 104 via the network 114. In certain example embodiments, the EHR vendor/aggregator 108 provides a single-point access for the electronic transmission of data and electronic requests associated with or using a healthcare provider's electronic medical records system to the service provider computer 104 via the prescriber/healthcare provider device 102.

The network 114 may include any telecommunication and/or data network, whether public, private, or a combination thereof, including a local area network, a wide area network, an intranet, the Internet, intermediate handheld data transfer devices, and/or any combination thereof and may be wired and/or wireless, or any combination thereof. The network 114 may also allow for real time, offline, and/or batch transactions to be transmitted between or among the prescriber/healthcare provider computer 102, the service provider computer 104, the EHR vendor/aggregator system 108, and the pharmacy claims processor computer 106. Various methodologies as described herein, may be practiced in the context of distributed computing environments. Although the service provider computer 104 is shown for simplicity as being in communication with the prescriber/healthcare provider device 102 (either directly or indirectly via the EHR vendor/aggregator system 108) or the pharmacy claims processor computer 106 via one intervening network 114, it is to be understood that any other network configurations are possible. For example, intervening network 114 may include a plurality of networks, each with devices such as gateways and routers for providing connectivity between or among the components of the system 100. Instead of or in addition to the network 114, dedicated communication links may be used to connect various devices in accordance with an example embodiment. For example, the service provider computer 104 may form the basis of network 114 that interconnects the prescriber/healthcare provider device 102 (either directly or indirectly via the EHR vendor/aggregator system 108), the service provider computer 104, and/or the pharmacy claims processor computer 106.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, the service provider computer 104 is implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2A:
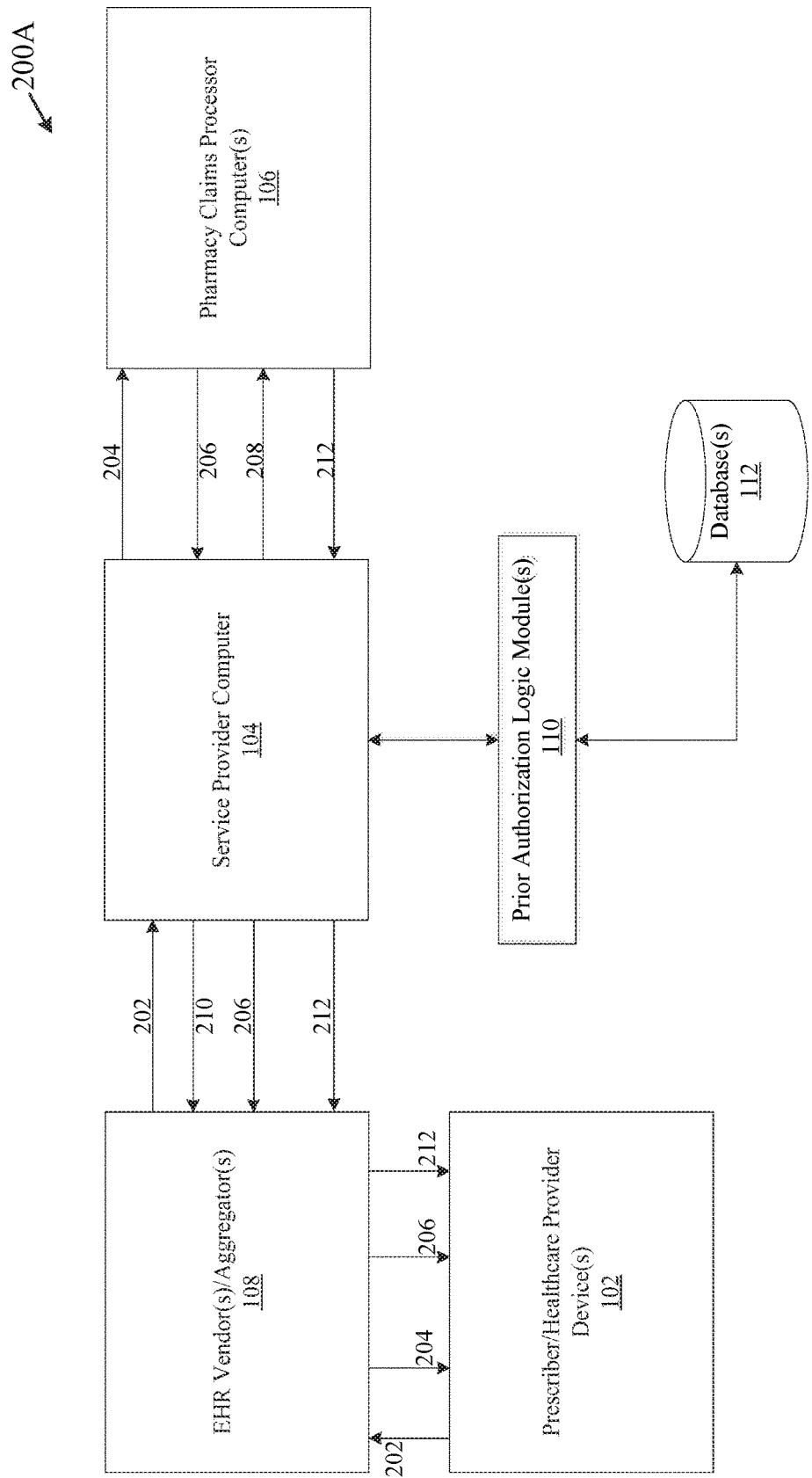
FIG. 2A is a diagram of an example system flow for providing improved prescription prior authorization services according to one exemplary embodiment.

FIG. 2A is a diagram of one example system flow 200A for an improved prescription prior authorization system provided as part of or in-line with the processing of an electronic prior authorization request through a service provider, such as through the service provider computer 104 illustrated in FIG. 1. FIGS. 3A-4B are flow charts of example methods 300 and 400 for implementing an improved prescription prior authorization system as part of the processing of the electronic prior authorization requests (e.g., an electronic prior authorization initiation request, an electronic prior authorization request, an electronic prior authorization appeal request, and/or an electronic prior authorization cancel request formatted according to the NCPDP Script Standard), in accordance with one example embodiment of the disclosure. The exemplary methods 300, 400, described below, may be performed by a suitable service provider computer 104 and/or prior authorization logic module 110. The exemplary methods 300, 400 will be described with reference to a physician as the prescriber; however, this is only for purposes of example as other healthcare prescribers and providers could be substituted for, and should each be individually read as being a part of each of these methods. As such, where the discussion of the methods below and the drawings state a physician or prescriber, any other healthcare prescriber or provider could be substituted, such as a nurse, physician's assistant, nurse practitioner, hospital, physician's office, clinic, healthcare center, pharmacists, pharmacy technicians, or any other person legally permitted to prescribe medications, products, or services to a patient. The exemplary methods 300, 400 described below will also be described with reference to an electronic prior authorization request generated by and electronically transmitted by the prescriber via the prescriber/healthcare provider device 102 to (either directly or indirectly via the EHR vendor/aggregator system 108) the service provider computer 104 and an electronic prior authorization response electronically transmitted from the pharmacy claims processor computer 1046 to the service provider computer in response to the electronic prior authorization request; however, this also is only for purposes of example as other electronic prior authorization requests (which may include, for example, (e.g., an electronic prior authorization initiation request, an electronic prior authorization request, an electronic prior authorization appeal request, and/or an electronic prior authorization cancel request formatted according to the NCPDP Script Standard) and other electronic prior authorization responses (which may include, for example, electronic prior authorization initiation response, electronic prior authorization response, electronic prior authorization appeal response, and electronic prior authorization cancel response formatted under the NCPDP Script Standard) could be substituted for these corresponding electronic prior authorization requests and electronic prior authorization responses and each form of electronic prior authorization request and electronic prior authorization response should each individually be read as being used in the methods described below.

Referring now to FIGS. 1, 2A, and 3A-B, the example method 300 begins at the START step and proceeds to step 302, where the prescriber or healthcare provider device, such as the prescriber/healthcare provider device 102, may optionally be utilized to capture a patient's pharmacy benefit information. In one example implementation, the healthcare provider device 102 may employ an electronic medical records (EMR) module 128 to capture the patient's pharmacy benefit information. The patient's pharmacy benefit information may be captured as a part of a patient visit. For example, the patient's pharmacy benefits information may include a payor identifier or pharmacy benefits identifier. For example, the patient's pharmacy benefit information may be captured as a part of an administrative function at the point of a patient admission (e.g., a patient registration). Alternatively, the patient's pharmacy benefit information may be captured at a time other than the patient visit. For example, the patient may communicate pharmacy benefit information utilizing a web-based portal from any patient-desired location. Generally, the patient pharmacy benefit information may be found on a patient's pharmacy benefit card (e.g., insurance card). In one non-limiting example, the EMR module 128 may capture, without limitation, a payor identifier or PBM identifier. Additional patient information not generally included on the patient's pharmacy benefit card that may be captured by the EMR includes, without limitation, a patient's date of birth and/or a patient gender code. While the step above describes the capture of the patient's pharmacy benefit information, this step is optional and may explicitly be excluded from the example method 300 in other example embodiments.

At step 304, a prescriber may select a medication, product, or service that has a prior authorization requirement for the patient. In one example, the medication, product, or service may include a medication identifier (e.g., an NDC code, RxNorm medication identifier, a medication name, etc.). At step 306 the prescriber/healthcare provider device 102 creates an electronic prior authorization request 202. In one example, the electronic prior authorization request 202 may be formatted according to the NCPDP Script Standard and the prescriber/healthcare provider device 102 may employ a provider benefit check module 132 to create the electronic prior authorization request 202. The electronic prior authorization request 202 may include, for example, the medication identifier (e.g., NDC code, RxNorm identifier, medication name) for each medication, product, or service to be dispensed, quantity for each of the medications, products, or services to be dispensed, days' supply for each of the medications, products, or services to be dispensed, the patient pharmacy benefit information (e.g., Banking Identification Number (BIN Number), BIN Number and Processor Control Number (PCN), or BIN Number and Group ID), patient information (e.g, patient first name, patient last name, patient date of birth, patient gender, patient zip or other postal code, Cardholder ID, Person Code etc.), a pharmacy identifier ((e.g., National Provider Identifier (NPI) code, DEA number, state license number, NCPDP Provider ID, store number, store name, and/or store address) for a patient's pharmacy of choice or the pharmacy from which a prior authorization request may have originated) as well as prescriber information (NPI code, DEA number, state license number, NCPDP Provider ID, prescriber name, prescriber address, prescriber zip or other postal code, etc). While the example embodiment describes including each of the patient information, patient pharmacy benefit information, medication identifier, and prescriber information into the electronic prior authorization request 202, each of these types of information may optionally not be included in the request 202 when it is created and transmitted to the service provider computer 104. In example embodiments where one or more of these types of information is not included in the electronic prior authorization request 202, the service provider computer 104 can evaluate historical prescription requests and/or prescription responses for the patient to identify the particular type of information (e.g., patient pharmacy benefit information, patient preferred pharmacy, patient identification information, etc.) and insert it into the electronic prior authorization request 202. In one example, the provider benefit check module 132 may automatically gather the patient pharmacy benefit information, patient information, and the prescriber information for insertion into the electronic prior authorization request 202.

At step 308, the prescriber/healthcare provider device 102 may format the electronic prior authorization request 202. For example, the prescriber/healthcare provider device 102 may employ the provider benefit check module 132 to format the electronic prior authorization request 202 in accordance with the NCPDP Script Standard. In one example, the provider benefit check module 132 may format the field and source of data included in the prescription benefit check transaction 202. For example:

Field: Source
Medication #: EMR module 126
Total Medications: EMR module 126
BIN Number: EMR module 126/patient pharmacy benefit card/patient profile
Processor Control Number: EMR module 126/patient pharmacy benefit card/patient profile
Pharmacy ID: EMR module 126/patient profile (e.g, NPI code DEA number, state license number, NCPDP Provider ID, pharmacy name, and/or pharmacy address)
Cardholder ID: EMR module 126/Patient pharmacy benefit card/patient profile
Group ID: EMR module 126/Patient pharmacy benefit card/patient profile
Person Code: EMR module 126/Patient pharmacy benefit card/patient profile
Date of Birth: EMR module 126/patient profile
Patient Gender Code: EMR module 126/patient profile (e.g., male or female)
Patient First Name: EMR module 126/Patient pharmacy benefit card/patient profile
Patient Last Name: EMR module 126/Patient pharmacy benefit card/patient profile
Product/Service ID (e.g., medication identifier) EMR module 126/patient profile (e.g., NDC code, RxNorm medication identifier, and/or medication/product/service name)
Prescriber ID: EMR module 126/prescriber profile (e.g., NPI code, DEA number, state license number, and/or NCPDP Provider ID)
Prescriber Last Name: EMR module 126/prescriber profile
Prescriber Address: EMR module 126/prescriber profile
Prescriber Postal Code: EMR module 126/prescriber profile At step 310, the prescriber/healthcare provider device 102 may electronically transmit (either directly or indirectly via the EHR vendor/aggregator system 108) the electronic prior authorization request 202 to the service provider computer 104. In one example embodiment, the prescriber/healthcare provider device 102 may employ the provider benefit check module 132 to electronically transmit the electronic prior authorization request 202 through the EHR vendor/aggregator system 108 and to the service provider computer 104 via one or more suitable networks 114 (e.g., a wide area network, the Internet, a cellular network, etc.). At step 312, the service provider computer 104 electronically receives the electronic prior authorization request 202 from the prescriber/healthcare provider device 102 via the EHR vendor/aggregator system 108 and the network 114.

At step 314, the service provider computer 104 may process the electronic prior authorization request 202. In one example, the service provider computer 104 may employ a prior authorization logic module 110 to process the electronic prior authorization request 202. In one example, the processing of the electronic prior authorization request 202 may include, without limitation, a determination of (i) whether all of the required patient, medication, and/or prescriber information is included in the electronic prior authorization request 202; (ii) whether the data in the electronic prior authorization request 202 is in a proper format; (iii) whether the prescriber identified in the electronic prior authorization request 202 is a supported prescriber; and/or (iv) whether the BIN Number or BIN Number and PCN or BIN Number and Group ID included in the electronic prior authorization request 202 is for a supported pharmacy claims processor computer 106 (e.g., supported PBM, insurer or prior authorization clearinghouse).

At step 316, the prior authorization logic module 110 or another portion of the service provider computer 104 can parse the electronic prior authorization request 202 to identify the one or more prescriber identifiers (e.g., NPI code, DEA number, state license number, NCPDP Provider ID, prescriber name, and/or prescriber zip code) that identifies the prescriber of the medication to the patient.

At step 318, the prior authorization logic module 110 or another portion of the service provider computer 104 can compare the identified prescriber identifier to a table, listing or schedule of prescriber identifiers in, for example, the database 112, for prescribers that are able to receive prior authorization evaluation review services to determine if the identified prescriber identifier from the electronic prior authorization request 202 matches at least one prescriber identifier for a supported prescriber receiving these services in the database 112. While the example embodiment describes evaluating the prescriber identifier, in other example embodiments the electronic prior authorization request 202 can include a vendor ID identifying the EHR vendor/aggregator system 108 and the module 110 or computer 104 can evaluate whether the EHR vendor/aggregator system 108 receives the prior authorization evaluation review services based on a comparison of the vendor ID.

At step 320, an inquiry is conducted to determine if the identified prescriber identifier in the electronic prior authorization request 202 matches at least one of the prescriber identifiers in at least one record of the database 112. In one example, the determination is made by the prior authorization logic module 110 or another portion of the service provider computer 104. In one example, if a match exists, it represents that the prescriber (or EHR vendor/aggregator system 108) identified by the prescriber identifier (or vendor ID) is able to receive prior authorization evaluation review services. If a match is not identified, then the NO branch is followed to step 350 of FIG. 3B. If a match to the identified prescriber identifier is determined, then the YES branch is followed to step 322.

At step 322, the prior authorization logic module 110 or another portion of the service provider computer 104 can parse the electronic prior authorization request 202 to identify the pharmacy claims processor identifier (e.g., destination identifier) in one or more predetermined fields of the electronic prior authorization request 202. The pharmacy claims processor identifier identifies the destination or pharmacy claims processor computer 106 associated with the pharmacy benefits provider providing pharmacy benefits to the patient or the prior authorization clearinghouse to receive the electronic prior authorization request 202. For example, the destination identifier or pharmacy claims processor identifier may be a BIN Number, BIN Number and PCN, or a BIN Number and Group ID.

At step 324, the prior authorization logic module 110 or another portion of the service provider computer 104 can compare the identified pharmacy claims processor identifier to a table, listing or schedule of pharmacy claims processor identifiers in, for example, the database 112, for pharmacy benefits providers, insurers, and/or prior authorization clearinghouses that receive prior authorization evaluation review services to determine if the identified pharmacy claims processor identifier from the electronic prior authorization request 202 matches at least one pharmacy claims processor identifier for a pharmacy benefits provider, insurer, or prior authorization clearinghouse in a record of the database 112.

At step 326, an inquiry is conducted to determine if the identified pharmacy claims processor identifier in the electronic prior authorization request 202 matches at least one of the pharmacy claims processor identifiers in a record of the database 112. In one example, the determination is made by the prior authorization logic module 110 or another portion of the service provider computer 104. In one example, if a match exists, it represents that the pharmacy benefits provider, insurer, or prior authorization clearinghouse identified by the pharmacy claims processor identifier is able to receive prior authorization evaluation review services. In another example embodiment, the pharmacy claims processor identifiers in the records of the database 112 may be for those pharmacy benefits providers, insurers, and/or prior authorization clearinghouses that do not receive prior authorization evaluation review services, and the match represents that the pharmacy benefits provider, insurer, or prior authorization clearinghouse identified by the pharmacy claims processor identifier is not to receive prior authorization evaluation review services. If a match is not identified, then the NO branch is followed to step 350 of FIG. 3B. If a match to the identified pharmacy claims processor identifier is determined, then the YES branch is followed to step 328.

At step 328, the prior authorization logic module 110 or another portion of the service provider computer 104 can parse the electronic prior authorization request 202 to identify the request type identifier in a predetermined field of the electronic prior authorization request 202. The request type identifier is a code that identifies to the service provider computer 104 and/or the prior authorization logic module 110 the type of request being received. In one example, there is a different code for each type of electronic prior authorization request, such as an electronic prior authorization initiation request, an electronic prior authorization request, an electronic prior authorization appeal request, and/or an electronic prior authorization cancel request formatted according to the NCPDP Script Standard. Further, each request type and associated request type identifier can be associated with a particular set of evaluation parameters or business rules for evaluating the associated electronic prior authorization request.

At step 330, the prior authorization logic module 110 or another portion of the service provider computer 104 can determine the evaluation parameters for evaluating the electronic prior authorization request based at least on the request type identifier. For example, the prior authorization logic module 110 or another portion of the service provider computer 104 can compare the request type identifier to a table, listing or schedule of records containing request type identifiers and associated evaluation parameters in, for example, the database 112 to identify a record with a matching request type identifier. Once the record with the matching request type identifier is identified, the prior authorization logic module 110 or another portion of the service provider computer 104 can retrieve the evaluation parameters or business rules for that particular request type.

In certain example embodiments, the evaluation parameters can include a requirement that particular fields in the electronic prior authorization request 202 include data therein as part of the request 202 before the request 202 will be forwarded to the pharmacy claims processor computer 106 for processing. Any one of the fields listed above or any additional fields that are added or are a part of the electronic prior authorization request may or may not be a required field that must include data. In certain example embodiments, if at least one of the fields requiring data (a "required data field") does not include data or does not include data in an expected format (e.g., text data provided but number expected, number data provided but text data expected, 3-digit number provided but 5-digit number expected, etc.) the prior authorization logic module 110 or another portion of the service provider computer 104 can generate a denial of the electronic prior authorization request 202 and can generate an electronic prior authorization response 204 that includes all or a portion of the information in the electronic prior authorization request 202, the denial, the reason for the denial, and optionally additional medication related or patient related messaging before electronically transmitting the electronic prior authorization response 204 back (either directly or indirectly via the EHR vendor/aggregator system 108) to the prescriber/healthcare provider computer 102.

Alternatively, the prior authorization logic module 110 or another portion of the service provider computer 104 can modify the violating fields (e.g., the required data fields that do not include data or include data in the incorrect format) of the electronic prior authorization request 202 to include data or to change the data from data in the incorrect format to data in the correct format before electronically transmitting the electronic prior authorization request 202 to the pharmacy claims processor computer 106 for processing.

For example, at step 332, the prior authorization logic module 110 or another portion of the service provider computer 104 can identify the patient demographic data fields (e.g., patient first name, patient last name, patient gender, patient date of birth, patient zip code, etc.) that require data in the electronic prior authorization request 202 based on a review of the identified evaluation parameters. The prior authorization logic module 110 or another portion of the service provider computer 104 can parse each of the required data fields in the patient demographic data fields of the electronic prior authorization request 202 to determine if it includes data in that particular data field at step 334.

At step 336, an inquiry is conducted to determine if the prior authorization logic module 110 or another portion of the service provider computer 104 identified any required data fields for patient demographic data that did not include data in the electronic prior authorization request. If one or more of the required data fields for patient demographic data did not include data as required, then the NO branch can be followed to step 364 of FIG. 3B. If all of the required data fields for patient demographic data included data, then the YES branch can be followed to step 338.

At step 338, the prior authorization logic module 110 or another portion of the service provider computer 104 can parse all or a portion of the data fields in the electronic prior authorization request 202 (e.g., the patient demographic data fields) and can identify the data format for the data in each of those fields. At step 340, the prior authorization logic module 110 or another portion of the service provider computer 104 can compare the data format for the data in each field of the electronic prior authorization request 202 to the expected data format for each particular field (e.g., identified from the identified evaluation parameters for the request type) to determine if the actual data format matches or otherwise satisfies the expected data format. For example, if the actual data in the patient gender field was numerical and the expected data format was for alphabetical data (e.g., M, F), then the actual data format would not satisfy the expected data format. In another example, if the actual data in the patient zip code field includes three numbers and the expected data format for the patient zip code field is five numbers, then the actual data format would not satisfy the expected data format.

At step 342, an inquiry is conducted to determine if the prior authorization logic module 110 or another portion of the service provider computer 104 identified any data fields in the electronic prior authorization request 202 that included data that was not in the correct format. If one or more of the data fields for patient demographic data or any other data fields in the request 202 included data that was not in the correct format, the NO branch can be followed to step 364 of FIG. 3B. If all of the data fields that included data in the patient demographic data fields or any other data fields in the request 202 were in the correct format, then the YES branch can be followed to step 344.

At step 344, the prior authorization logic module 110 or another portion of the service provider computer 104 can parse the electronic prior authorization request 202 to identify the diagnosis code in a predetermined field of the electronic prior authorization request 202. In one example embodiment, the diagnosis code identifies the illness or malady of the patient and further provides a basis for the medication/product/service that has been prescribed to the patient. For example, the diagnosis code may be an International Classes of Diseases (ICD) diagnosis code (e.g., ICD-9 or ICD-10).

At step 346, the prior authorization logic module 110 or another portion of the service provider computer 104 can compare the identified diagnosis code in the electronic prior authorization request 202 to a table, listing or schedule of valid diagnosis codes records containing valid diagnosis codes in, for example, the database 112, to determine if the identified diagnosis code from the electronic prior authorization request 202 matches at least one valid diagnosis code in a record of the database 112.

At step 348, an inquiry is conducted to determine if the identified diagnosis code in the electronic prior authorization request 202 matches at least one of the valid diagnosis codes in a record of the database 112. In one example, the determination is made by the prior authorization logic module 110 or another portion of the service provider computer 104. In one example, if a match exists, it represents that the diagnosis code in the electronic prior authorization request 202 is a valid diagnosis code for a prior authorization request. If a match is not identified, then the NO branch is followed to step 364 of FIG. 3B. If a match to the identified diagnosis code is determined, then the YES branch is followed to step 350.

At step 350, the service provider computer 104 can electronically transmit the electronic prior authorization request 202 to the pharmacy claims processor computer 106 based on, for example the pharmacy claims processor identifier (destination identifier) (e.g., the BIN Number, BIN Number and PCN, or BIN Number and Group ID) in the electronic prior authorization request 202. For example, the service provider computer 104 can electronically transmit the electronic prior authorization request 202 to the pharmacy claims processor computer 106 via the network 114.

At step 352, the pharmacy claims processor computer 106 can electronically receive the electronic prior authorization request 202 from the service provider computer 104 via, for example, the network 114. At step 354, the pharmacy claims processor computer 106 may process the electronic prior authorization request 202 and generate an electronic prior authorization response 206. In one example embodiment, the electronic prior authorization response 206 to the electronic prior authorization request 202 may include a determination by the pharmacy claims processor computer 106, insurer, PBM, prior authorization clearinghouse or the like, of whether the electronic prior authorization request 202 was approved or denied, and if denied, what the basis of the denial was (e.g., via a denial code). At step 356, the pharmacy claims processor computer 106 may electronically transmit the electronic prior authorization response 206 to the service provider computer 104 via, for example, the network 114. The electronic prior authorization response 206 may also include, without limitation, a transaction response type (e.g., electronic prior authorization initiation response, electronic prior authorization response, electronic prior authorization appeal response, and electronic prior authorization cancel response formatted under the NCPDP Script Standard) and/or a transaction status indicator associated with whether the electronic prior authorization request 202 was approved or denied. In one example embodiment, when the electronic prior authorization request 202 is approved, the electronic prior authorization response 206 may have a transaction status indicator of "B". If, however, the electronic prior authorization request 202 is denied, the electronic prior authorization response 206 may have a transaction indicator of "R". The electronic prior authorization response 206 may further include all or any portion of the data from the electronic prior authorization request 202.

In one example, if the electronic prior authorization response 206 includes the status indicator "R", the electronic prior authorization response 206 may also include one or more fields that include a denial reason field populated with a denial code identifying the reason that the electronic prior authorization request 202 was denied, a reason for service code field populated with a denial error code, and/or a reason for service description field populated with an abbreviated description of the corresponding reason for service code.

At step 358, the service provider computer 104 can electronically receive the electronic prior authorization response 206 from the pharmacy claims processor computer 106 via, for example, the network 114. At step 360, the prior authorization logic module 110 or another portion of the service provider computer 104 can electronically transmit all or a portion of the electronic prior authorization response 206 either directly to the prescriber/healthcare provider device 102 or indirectly through the EHR vendor/aggregator system 108 and to the prescriber/healthcare provider device 102 from which the electronic prior authorization request 202 originated. In one example, the electronic prior authorization response 206 is electronically transmitted from the service provider computer 104 through the EHR vendor/aggregator system 108 and to the prescriber/healthcare provider device via the network 114. The electronic prior authorization response 206 can be received by the prescriber/healthcare provider device via the EHR vendor/aggregator system 108 at step 362, wherein the contents of the response 206 can be visually displayed on a monitor or screen communicably coupled to the prescriber/healthcare provider device 102 for review by the prescriber, other healthcare provider or an employee of the prescriber or healthcare provider. The process can then continue to the END step.

Returning to the inquiries at steps 336, 342, and 348, the NO step is followed to step 364, where the prior authorization logic module 110 or another portion of the service provider computer 104 can automatically generate a denial of delivery of the electronic prior authorization request 202. In one example, the denial of delivery of the electronic prior authorization request 240 is generated by the prior authorization logic module 110 or another portion of the service provider computer 104. At step 366, the prior authorization logic module 110 or another portion of the service provider computer 104 can generate a message identifying the basis of the denial of delivery of the electronic prior authorization request 202. For example, the message may include an explanation that the denial is due to required data not being included in required data fields of the electronic prior authorization request 202, that the denial is due to the data in one or more data fields of the electronic prior authorization request 202 being in the wrong format, and/or that the denial is due to the diagnosis code being incorrect in the electronic prior authorization request 202.

The prior authorization logic module 110 or another portion of the service provider computer 104 can insert the denial message into one or more fields (e.g., a text field) of the denial of delivery of the electronic prior authorization request 204 at step 368. At step 370, the prior authorization logic module 110 or another portion of the service provider computer 104 can electronically transmit the denial of delivery of the electronic prior authorization request 204 either directly to the prescriber/healthcare provider device 102 or indirectly through the EHR vendor/aggregator system 108 and to the prescriber/healthcare provider device 102 from which the electronic prior authorization request 202 originated. In one example, the denial of delivery of the electronic prior authorization request 204 is electronically transmitted from the service provider computer 104 through the EHR vendor/aggregator system 108 and to the prescriber/healthcare provider device via the network 114. The denial of delivery of the electronic prior authorization request 204 can be received by the prescriber/healthcare provider device via the EHR vendor/aggregator system 108 at step 372, wherein the contents of the response 204 can be visually displayed on a monitor or screen communicably coupled to the prescriber/healthcare provider device 102 for review by the prescriber, other healthcare provider or an employee of the prescriber or healthcare provider. The process can then continue to the END step.

Figure 4A:
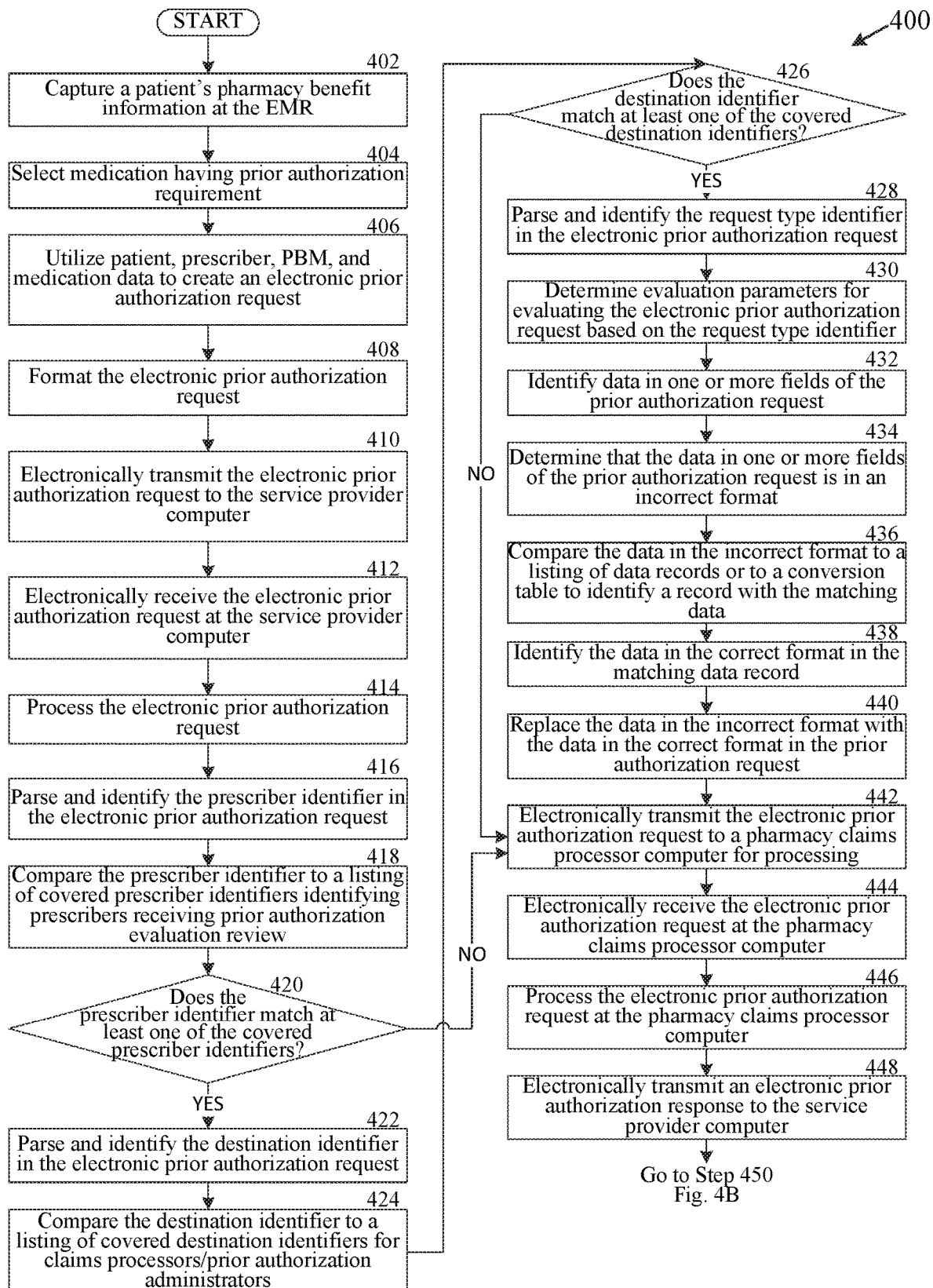
FIGS. 4A-B are another example methodology for implementing an improved prior authorization system, in accordance with one exemplary embodiment.
Figure 4B:
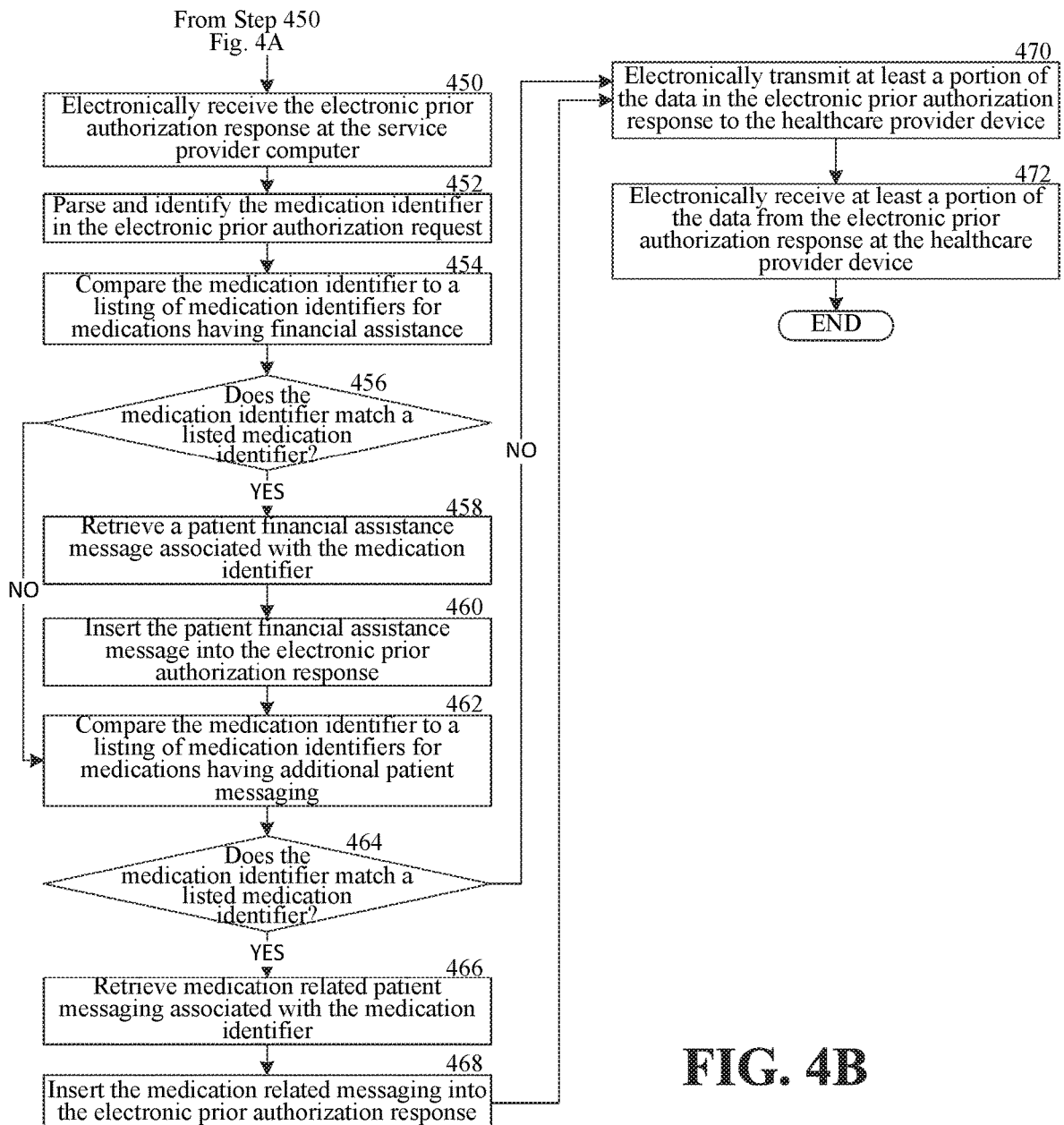

FIG. 4 is another example methodology for implementing an improved prior authorization system, in accordance with one example embodiment of the disclosure. Referring now to FIGS. 1, 2A, and 4, the example method 400 begins at the START step and proceeds to step 402, where the prescriber or healthcare provider device, such as the prescriber/healthcare provider device 102, may optionally be utilized to capture a patient's pharmacy benefit information. In one example implementation, the healthcare provider device 102 may employ an electronic medical records (EMR) module 128 to capture the patient's pharmacy benefit information. The patient's pharmacy benefit information may be captured as a part of a patient visit. For example, the patient's pharmacy benefit information may be captured as a part of an administrative function at the point of a patient admission (e.g., a patient registration). Alternatively, the patient's pharmacy benefit information may be captured at a time other than the patient visit. For example, the patient may communicate pharmacy benefit information utilizing a web-based portal from any patient-desired location. Generally, the patient pharmacy benefit information may be found on a patient's pharmacy benefit card (e.g., insurance card). In one example, the EMR module 128 may capture from a patient's pharmacy benefit card, without limitation, a BIN Number, a Processor Control Number, an assigned Cardholder ID, Person Code, Relationship Code, and/or a Group ID. Additional patient information not generally included on the patient's pharmacy benefit card that may be captured by the EMR includes, without limitation, a patient's date of birth and/or a patient gender code. While the step above describes the capture of the patient's pharmacy benefit information, this step is optional and may explicitly be excluded from the example method 400 in other example embodiments.

At step 404, a prescriber may select a medication, product, or service that has a prior authorization requirement for the patient. In one example, the medication, product, or service may include a medication identifier (e.g., an NDC code, RxNorm medication identifier, a medication name, etc.). At step 406 the prescriber/healthcare provider device 102 creates an electronic prior authorization request 202. In one example, the electronic prior authorization request 202 may be formatted according to the NCPDP Script Standard and the prescriber/healthcare provider device 102 may employ a provider benefit check module 132 to create the electronic prior authorization request 202. The electronic prior authorization request 202 may include, for example, the medication identifier (e.g., NDC code, RxNorm identifier, medication name) for each medication, product, or service to be dispensed, quantity for each of the medications, products, or services to be dispensed, days' supply for each of the medications, products, or services to be dispensed, the patient pharmacy benefit information (e.g., Banking Identification Number (BIN Number), BIN Number and Processor Control Number (PCN), or BIN Number and Group ID), patient information (e.g, patient first name, patient last name, patient date of birth, patient gender, patient zip or other postal code, Cardholder ID, Person Code etc.), a pharmacy identifier ((e.g., National Provider Identifier (NPI) code, DEA number, state license number, NCPDP Provider ID, store number, store name, and/or store address) for a patient's pharmacy of choice or the pharmacy from which a prior authorization request may have originated) as well as prescriber information (NPI code, DEA number, state license number, NCPDP Provider ID, prescriber name, prescriber address, prescriber zip or other postal code, etc). While the example embodiment describes including each of the patient information, patient pharmacy benefit information, medication identifier, and prescriber information into the electronic prior authorization request 202, each of these types of information may optionally not be included in the request 202 when it is created and transmitted to the service provider computer 104. In example embodiments where one or more of these types of information is not included in the electronic prior authorization request 202, the service provider computer 104 can evaluate historical prescription requests and/or prescription responses for the patient to identify the particular type of information (e.g., patient pharmacy benefit information, patient preferred pharmacy, patient identification information, etc.) and insert it into the electronic prior authorization request 202. In one example, the provider benefit check module 132 may automatically gather the patient pharmacy benefit information, patient information, and the prescriber information for insertion into the electronic prior authorization request 202.

At step 408, the prescriber/healthcare provider device 102 may format the electronic prior authorization request 202. For example, the prescriber/healthcare provider device 102 may employ the provider benefit check module 132 to format the electronic prior authorization request 202 in accordance with the NCPDP Script Standard. In one example, the provider benefit check module 132 may format the field and source of data included in the prescription benefit check transaction 202. For example:

Field: Source
Medication #: EMR module 126
Total Medications: EMR module 126
BIN Number: EMR module 126/patient pharmacy benefit card/patient profile
Processor Control Number: EMR module 126/patient pharmacy benefit card/patient profile
Pharmacy ID: EMR module 126/patient profile (e.g, NPI code DEA number, state license number, NCPDP Provider ID, pharmacy name, and/or pharmacy address)
Cardholder ID: EMR module 126/Patient pharmacy benefit card/patient profile
Group ID: EMR module 126/Patient pharmacy benefit card/patient profile
Person Code: EMR module 126/Patient pharmacy benefit card/patient profile
Date of Birth: EMR module 126/patient profile
Patient Gender Code: EMR module 126/patient profile (e.g., male or female)
Patient First Name: EMR module 126/Patient pharmacy benefit card/patient profile
Patient Last Name: EMR module 126/Patient pharmacy benefit card/patient profile
Product/Service ID (e.g., medication identifier) EMR module 126/patient profile (e.g., NDC code, RxNorm medication identifier, and/or medication/product/service name)
Prescriber ID: EMR module 126/prescriber profile (e.g., NPI code, DEA number, state license number, and/or NCPDP Provider ID)
Prescriber Last Name: EMR module 126/prescriber profile
Prescriber Address: EMR module 126/prescriber profile
Prescriber Postal Code: EMR module 126/prescriber profile At step 410, the prescriber/healthcare provider device 102 may electronically transmit (either directly or indirectly via the EHR vendor/aggregator system 108) the electronic prior authorization request 202 to the service provider computer 104. In one example embodiment, the prescriber/healthcare provider device 102 may employ the provider benefit check module 132 to electronically transmit the electronic prior authorization request 202 through the EHR vendor/aggregator system 108 and to the service provider computer 104 via one or more suitable networks 114 (e.g., a wide area network, the Internet, a cellular network, etc.). At step 412, the service provider computer 104 electronically receives the electronic prior authorization request 202 from the prescriber/healthcare provider device 102 via the EHR vendor/aggregator system 108 and the network 114.

At step 414, the service provider computer 104 may process the electronic prior authorization request 202. In one example, the service provider computer 104 may employ a prior authorization logic module 110 to process the electronic prior authorization request 202. In one example, the processing of the electronic prior authorization request 202 may include, without limitation, a determination of (i) whether all of the required patient, medication, and/or prescriber information is included in the electronic prior authorization request 202; (ii) whether the data in the electronic prior authorization request 202 is in a proper format; (iii) whether the prescriber identified in the electronic prior authorization request 202 is a supported prescriber; and/or (iv) whether the BIN Number or BIN Number and PCN or BIN Number and Group ID included in the electronic prior authorization request 202 is for a supported pharmacy claims processor computer 106 (e.g., supported PBM, insurer or prior authorization clearinghouse).

At step 416, the prior authorization logic module 110 or another portion of the service provider computer 104 can parse the electronic prior authorization request 202 to identify the one or more prescriber identifiers (e.g., NPI code, DEA number, state license number, NCPDP Provider ID, prescriber name, and/or prescriber zip code) that identifies the prescriber of the medication to the patient.

At step 418, the prior authorization logic module 110 or another portion of the service provider computer 104 can compare the identified prescriber identifier to a table, listing or schedule of prescriber identifiers in, for example, the database 112, for prescribers that are able to receive prior authorization evaluation review services to determine if the identified prescriber identifier from the electronic prior authorization request 202 matches at least one prescriber identifier for a supported prescriber receiving these services in the database 112. While the example embodiment describes evaluating the prescriber identifier, in other example embodiments the electronic prior authorization request 202 can include a vendor ID identifying the EHR vendor/aggregator system 108 and the module 110 or computer 104 can evaluate whether the EHR vendor/aggregator system 108 receives the prior authorization evaluation review services based on a comparison of the vendor ID.

At step 420, an inquiry is conducted to determine if the identified prescriber identifier in the electronic prior authorization request 202 matches at least one of the prescriber identifiers in at least one record of the database 112. In one example, the determination is made by the prior authorization logic module 110 or another portion of the service provider computer 104. In one example, if a match exists, it represents that the prescriber (or EHR vendor/aggregator system 108) identified by the prescriber identifier (or vendor ID) is able to receive prior authorization evaluation review services. If a match is not identified, then the NO branch is followed to step 442. If a match to the identified prescriber identifier is determined, then the YES branch is followed to step 422.

At step 422, the prior authorization logic module 110 or another portion of the service provider computer 104 can parse the electronic prior authorization request 202 to identify the pharmacy claims processor identifier (e.g., destination identifier) in one or more predetermined fields of the electronic prior authorization request 202. The pharmacy claims processor identifier identifies the destination or pharmacy claims processor computer 106 associated with the pharmacy benefits provider providing pharmacy benefits to the patient or the prior authorization clearinghouse to receive the electronic prior authorization request 202. For example, the destination identifier or pharmacy claims processor identifier may be a BIN Number, BIN Number and PCN, or a BIN Number and Group ID.

At step 424, the prior authorization logic module 110 or another portion of the service provider computer 104 can compare the identified pharmacy claims processor identifier to a table, listing or schedule of pharmacy claims processor identifiers in, for example, the database 112, for pharmacy benefits providers, insurers, and/or prior authorization clearinghouses that receive prior authorization evaluation review services to determine if the identified pharmacy claims processor identifier from the electronic prior authorization request 202 matches at least one pharmacy claims processor identifier for a pharmacy benefits provider, insurer, or prior authorization clearinghouse in a record of the database 112.

At step 426, an inquiry is conducted to determine if the identified pharmacy claims processor identifier in the electronic prior authorization request 202 matches at least one of the pharmacy claims processor identifiers in a record of the database 112. In one example, the determination is made by the prior authorization logic module 110 or another portion of the service provider computer 104. In one example, if a match exists, it represents that the pharmacy benefits provider, insurer, or prior authorization clearinghouse identified by the pharmacy claims processor identifier is able to receive prior authorization evaluation review services. In another example embodiment, the pharmacy claims processor identifiers in the records of the database 112 may be for those pharmacy benefits providers, insurers, and/or prior authorization clearinghouses that do not receive prior authorization evaluation review services, and the match represents that the pharmacy benefits provider, insurer, or prior authorization clearinghouse identified by the pharmacy claims processor identifier is not to receive prior authorization evaluation review services. If a match is not identified, then the NO branch is followed to step 442. If a match to the identified pharmacy claims processor identifier is determined, then the YES branch is followed to step 428.

At step 428, the prior authorization logic module 110 or another portion of the service provider computer 104 can parse the electronic prior authorization request 202 to identify the request type identifier in a predetermined field of the electronic prior authorization request 202. The request type identifier is a code that identifies to the service provider computer 104 and/or the prior authorization logic module 110 the type of request being received. In one example, there is a different code for each type of electronic prior authorization request, such as an electronic prior authorization initiation request, an electronic prior authorization request, an electronic prior authorization appeal request, and/or an electronic prior authorization cancel request formatted according to the NCPDP Script Standard. Further, each request type and associated request type identifier can be associated with a particular set of evaluation parameters or business rules for evaluating the associated electronic prior authorization request.

At step 430, the prior authorization logic module 110 or another portion of the service provider computer 104 can determine the evaluation parameters for evaluating the electronic prior authorization request based at least on the request type identifier. For example, the prior authorization logic module 110 or another portion of the service provider computer 104 can compare the request type identifier to a table, listing or schedule of records containing request type identifiers and associated evaluation parameters in, for example, the database 112 to identify a record with a matching request type identifier. Once the record with the matching request type identifier is identified, the prior authorization logic module 110 or another portion of the service provider computer 104 can retrieve the evaluation parameters or business rules for that particular request type.

In certain example embodiments, the evaluation parameters can include a rule to evaluate the parameter type for each data field and in some cases conversion tables for converting data from one format (an incorrect format) to a different format (a correct format) before electronically transmitting the electronic prior authorization request 202 to the pharmacy claims processor computer 106 for processing. For example, the data in the medication identifier data field of the electronic prior authorization request 202 may be an RxNorm number when an NDC code is the more preferred or correct medication identifier format. The database 112 can include one or more conversion tables for converting the RxNorm number to an NDC code. In another example, the prescriber identifier or the pharmacy identifier in the electronic prior authorization request 202 may be in the format of a DEA number or state license number when an NPI code is the more preferred or correct prescriber identifier or pharmacy identifier. The database 112 can also include one or more conversion tables for converting the DEA number and/or the state license number to the NPI code for the prescriber or pharmacy. Other similar conversions are contemplated within the scope of this disclosure.

At step 432, the prior authorization logic module 110 or another portion of the service provider computer 104 can identify data in one or more fields of the electronic prior authorization request 202. The prior authorization logic module 110 or another portion of the service provider computer 104 can determine that the data in the one or more fields of the electronic prior authorization request 202 is in an incorrect format. For example, the prior authorization logic module 110 can evaluate the data in a particular data field to determine the format and compare it to one or more identified evaluation parameters for that data field to determine that the format of the data in the data field is incorrect. The prior authorization logic module 110 can further determine, for example based on the evaluation parameters, that the proper format for the current data in the particular data field can be obtained via one or more conversion tables. For example, the prior authorization logic module 110 may evaluate the data in the medication identifier data field of the electronic prior authorization request 202 and determine that it is in the form of an RxNorm number. The prior authorization logic module 110 may determine based on the one or more evaluation parameters that the medication identifier should be in the format of an NDC code and that conversion tables are provided for converting the RxNorm number to an NDC code. In another example, the prior authorization logic module 110 may evaluate the data in the prescriber identifier data field and/or the pharmacy identifier data field in the electronic prior authorization request 202 and determine that the data in the prescriber identifier data field and/or the pharmacy identifier data field is in the form of one or more of a DEA number, state license number, and/or NCPDP Provider ID. The prior authorization logic module 110 may determine based on the one or more evaluation parameters that the prescriber identifier and/or the pharmacy identifier should be in the format of an NPI code and that conversion tables are provided for converting the DEA number, state license number, and/or NCPDP Provider ID to an NPI code identifying the particular prescriber and/or pharmacy.

At step 436, the prior authorization logic module 110 or another portion of the service provider computer 104 can compare the data in the particular field that is in the incorrect format to a listing of data records or conversion tables for that type of data to identify a record or corresponding element on the conversion table that matches the data that is in the incorrect format. The prior authorization logic module 110 or another portion of the service provider computer 104 can identify the data in the correct format by, for example finding the correctly formatted data in the matching record of the conversion table at step 438. At step 440, the prior authorization logic module 110 or another portion of the service provider computer 104 can replace the data of the incorrect format in the particular data field of the electronic prior authorization request with the identified data in the correct format thereby creating a modified electronic prior authorization request 208. For example, the prior authorization logic module 110 can remove the RxNorm number from the medication identifier data field of the electronic prior authorization request 202 and automatically insert the NDC code corresponding to the RxNorm number into the medication identifier data field to create a modified electronic prior authorization request 208. In another example, the prior authorization logic module 110 can remove the DEA number from the prescriber identifier data field of the electronic prior authorization request 202 and automatically insert the NPI code corresponding to the DEA number into the prescriber identifier data field to create a modified electronic prior authorization request 208. In another example, the prior authorization logic module 110 can remove the state license number from the pharmacy identifier data field of the electronic prior authorization request 202 and automatically insert the NPI code corresponding to the state license number into the pharmacy identifier data field to create a modified electronic prior authorization request 208.

At step 442, the service provider computer 104 can electronically transmit the electronic prior authorization request 202/modified electronic prior authorization request 208 to the pharmacy claims processor computer 106 based on, for example the pharmacy claims processor identifier (destination identifier) (e.g., the BIN Number, BIN Number and PCN, or BIN Number and Group ID) in the electronic prior authorization request 202. For example, the service provider computer 104 can electronically transmit the electronic prior authorization request 202/modified electronic prior authorization request 208 to the pharmacy claims processor computer 106 via the network 114.

At step 444, the pharmacy claims processor computer 106 can electronically receive the electronic prior authorization request 202/modified electronic prior authorization request 208 from the service provider computer 104 via, for example, the network 114. At step 446, the pharmacy claims processor computer 106 may process the electronic prior authorization request 202/modified electronic prior authorization request 208 and generate an electronic prior authorization response 212. In one example embodiment, the electronic prior authorization response 212 to the electronic prior authorization request 202/modified electronic prior authorization request 208 may include a determination by the pharmacy claims processor computer 106, insurer, PBM, prior authorization clearinghouse or the like, of whether the electronic prior authorization request 202/modified electronic prior authorization request 208 was approved or denied, and if denied, what the basis of the denial was (e.g., via a denial code). At step 448, the pharmacy claims processor computer 106 may electronically transmit the electronic prior authorization response 212 to the service provider computer 104 via, for example, the network 114. The electronic prior authorization response 212 may also include, without limitation, a transaction response type (e.g., electronic prior authorization initiation response, electronic prior authorization response, electronic prior authorization appeal response, and electronic prior authorization cancel response formatted under the NCPDP Script Standard) and/or a transaction status indicator associated with whether the electronic prior authorization request 202/modified electronic prior authorization request 208 was approved or denied. In one example embodiment, when the electronic prior authorization request 202/modified electronic prior authorization request 208 is approved, the electronic prior authorization response 212 may have a transaction status indicator of "B". If, however, the electronic prior authorization request 202/modified electronic prior authorization request 208 is denied, the electronic prior authorization response 212 may have a transaction indicator of "R". The electronic prior authorization response 212 may further include all or any portion of the data from the electronic prior authorization request 202/modified electronic prior authorization request 208.

In one example, if the electronic prior authorization response 212 includes the status indicator "R", the electronic prior authorization response 212 may also include one or more fields that include a denial reason field populated with a denial code identifying the reason that the electronic prior authorization request 202/modified electronic prior authorization request 208 was denied, a reason for service code field populated with a denial error code, and/or a reason for service description field populated with an abbreviated description of the corresponding reason for service code.

At step 450, the service provider computer 104 can electronically receive the electronic prior authorization response 212 from the pharmacy claims processor computer 106 via, for example, the network 114. The prior authorization logic module 110 or another portion of the service provider computer 104 can also determine if financial assistance is provided for the medication identified in the electronic prior authorization response 212. The financial assistance can be provided for those requests 202, 208 that have been denied as well as those requests 202, 208 that have been approved to cover all or a portion of the patient pay amount in order to assist the patient in receiving the medication prescribed by the prescriber. For example, at step 452, the prior authorization logic module 110 or another portion of the service provider computer 104 can parse the electronic prior authorization response 212 to identify the medication identifiers (e.g., NDC code, RxNorm medication identifier, or medication name) that identifies the medication/product/service prescribed to the patient.

At step 454, the prior authorization logic module 110 or another portion of the service provider computer 104 can compare the identified medication identifier to a table, listing or schedule of medication identifiers in, for example, the database 112, for medications that are associated with financial assistance opportunities that provide financial assistance to the patients prescribed that medication and wherein the financial assistance is provided by non-insurance entities (e.g., manufacturers and/or marketers of the medications/products/services prescribed to patients). The comparison is made to determine if the identified medication identifier from the electronic prior authorization response 212 matches at least one medication identifier for medications that are associated with financial assistance opportunities that provide financial assistance to the patients prescribed that medication from non-insurance entities in the database 112.

At step 456, an inquiry is conducted to determine if the identified medication identifier in the electronic prior authorization response 212 matches at least one of the medication identifiers in at least one record of the database 112. In one example, the determination is made by the prior authorization logic module 110 or another portion of the service provider computer 104. In one example, if a match exists, it represents that a non-insurance based financial assistance opportunity that reduces and/or eliminates the patient financial responsibility for the medication is available to the patient prescribed the medication identified by the medication identifier. If a match is not identified, then the NO branch is followed to step 462. If a match to the identified medication identifier is determined, then the YES branch is followed to step 458, wherein the prior authorization logic module 110 or another portion of the service provider computer 104 can retrieve a patient financial assistance message in, for example, the matching record that is associated with the medication identifier in the response 212 and explains the non-insurance based financial assistance opportunity to the prescriber and/or patient. At step 460, the prior authorization logic module 110 or another portion of the service provider computer 104 can insert the patient financial assistance message into the electronic prior authorization response 212.

At step 462, the prior authorization logic module 110 or another portion of the service provider computer 104 can compare the identified medication identifier to a table, listing or schedule of medication identifiers in, for example, the database 112, for additional messaging related to the medication or patient identified in the electronic prior authorization request 202, 208 or response 212. Alternatively, the one or more patient identifiers from the request 202, 208 or response 212 may be identified and compared to a table, schedule, or listing or patient identifiers in the database 112 to determine if a match exists. The comparison is made to determine if the identified medication identifier and/or patient identifiers from the electronic prior authorization request 202, 208 or response 212 match at least one medication identifier for medications or the patient identifiers for a patient that are associated with addition medication or patient-related messaging. The medication or patient-related messaging can include, but is not limited to, a risk evaluation mitigation strategies (REMS) message.

At step 464, an inquiry is conducted to determine if the identified medication identifier in the electronic prior authorization request 202, 208 or response 212 matches at least one of the medication identifiers in at least one record of the database 112 and/or if the patient identifier in the electronic prior authorization request 202, 208 or response 212 matches at least one of the patient identifiers in at least one record of the database 112 for that patient. In one example, the determination is made by the prior authorization logic module 110 or another portion of the service provider computer 104. In one example, if a match exists, it represents that additional medication and/or patient related messaging is available for the patient identified in the electronic prior authorization request 202, 208. If a match is not identified, then the NO branch is followed to step 470. If a match to the identified medication identifier and or patient identifier(s) is determined, then the YES branch is followed to step 466, where the prior authorization logic module 110 or another portion of the service provider computer 104 can retrieve the additional medication or patient-related message in, for example, the matching record that is associated with the medication identifier and/or patient identifier(s).

At step 468, the prior authorization logic module 110 or another portion of the service provider computer 104 can insert the medication and/or patient-related message into the electronic prior authorization response 212. At step 470, the prior authorization logic module 110 or another portion of the service provider computer 104 can electronically transmit all or a portion of the electronic prior authorization response 212 either directly to the prescriber/healthcare provider device 102 or indirectly through the EHR vendor/aggregator system 108 and to the prescriber/healthcare provider device 102 from which the electronic prior authorization request 202 originated. In one example, the electronic prior authorization response 212 is electronically transmitted from the service provider computer 104 through the EHR vendor/aggregator system 108 and to the prescriber/healthcare provider device 102 via the network 114. The electronic prior authorization response 212 can be received by the prescriber/healthcare provider device 102 via the EHR vendor/aggregator system 108 at step 372, where the contents of the response 206 can be visually displayed on a monitor or screen communicably coupled to the prescriber/healthcare provider device 102 for review by the prescriber, patient other healthcare provider or an employee of the prescriber or healthcare provider. The process can then continue to the END step.

The methods described and shown in FIGS. 3A-4B may be carried out or performed in any suitable order as desired in various embodiments. Additionally, in certain example embodiments, at least a portion of the operations may be carried out in parallel. Furthermore, in certain example embodiments, less than or more than the operations described in FIGS. 3A-4B may be performed.

Figure 2B:
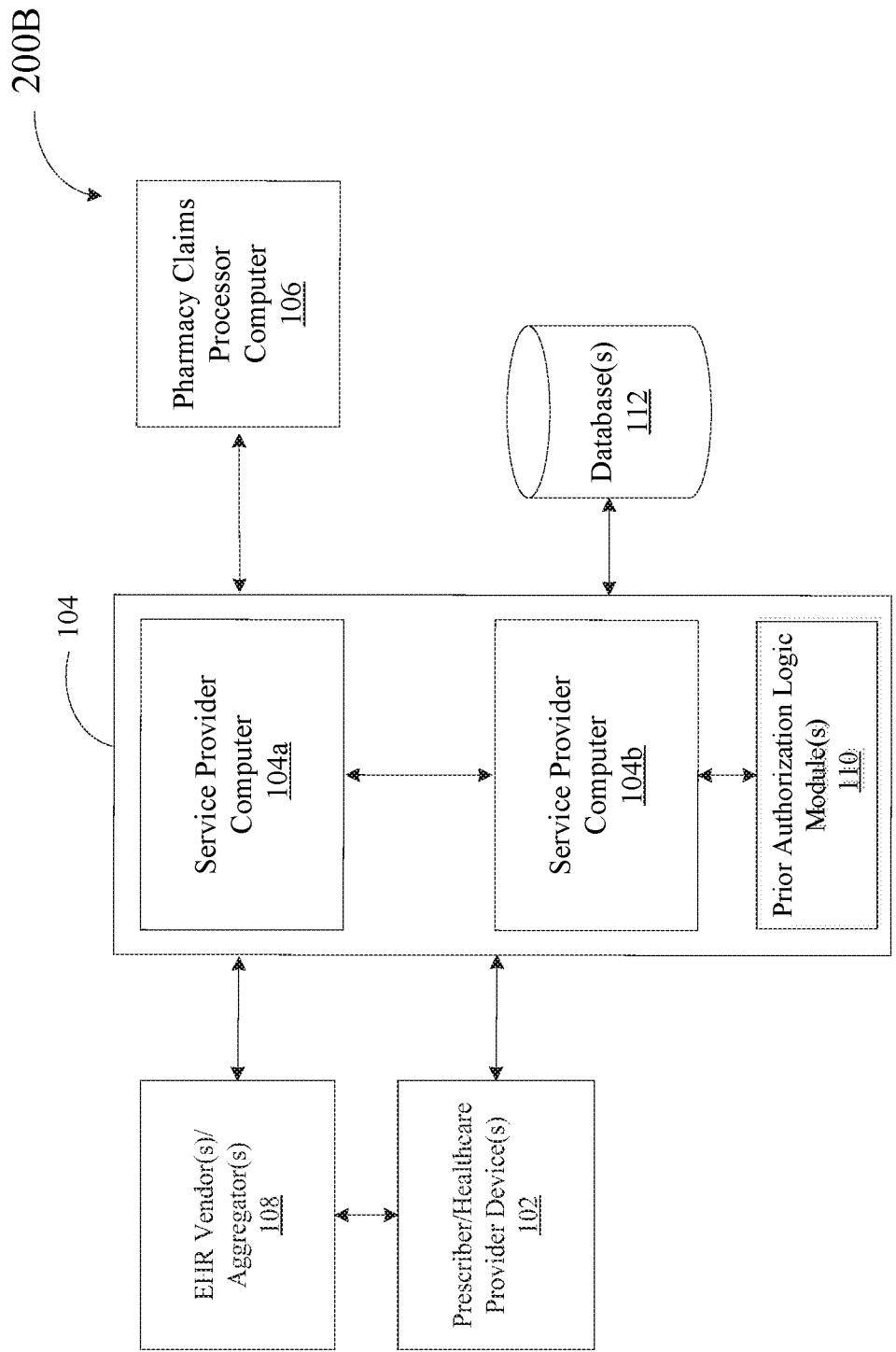
FIG. 2B is a diagram of an alternative example system flow for providing improved prescription prior authorization services according to another example embodiment.
Figure 3B:
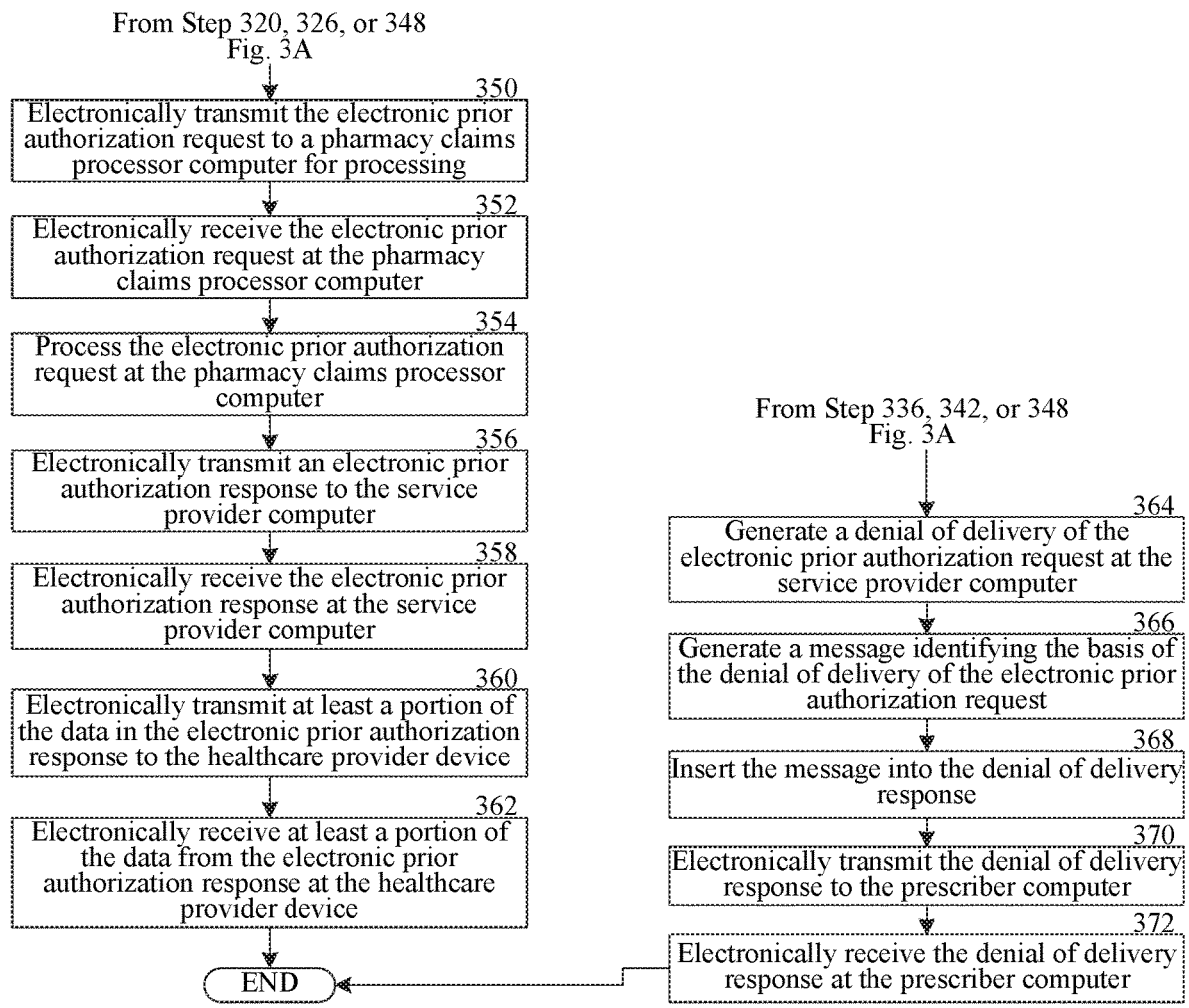

Likewise, while FIGS. 3A-4B have been described primarily in conjunction with FIG. 2A, it will be appreciated that variations of FIG. 2A are available. As shown by the system 200B of FIG. 2B, the service provider computer 104 may include two or more distinct service provider computers 104a and 104b that are in communication with each other.

These distinct service provider computers 104a and 104b may be owned, operated, and or located by the same or distinct and wholly-unrelated companies. The service provider computer 104a may be operative with the prescriber/healthcare provider device 102 and EHR vendor/aggregator systems 108, while the service provider computer 104b may be operative with other prescriber/healthcare provider devices, EHR vendor/aggregator systems, and/or pharmacy claims processor computers. However, the service provider computer 104b may have a prescription prior authorization processing arrangement with the service provider computer 104a. Under the prescription prior authorization processing arrangement, the service provider computer 104a may be permitted to utilize or offer services of the service provider computer 104b, including the operations and use of the prior authorization logic module 110 and the data in the database 112 to provide improved prior authorization review and editing services as discussed above. Accordingly, the services accessible by the service provider computer 104b may be available to the prescriber/healthcare provider device 102 via the service provider computers 104a and 104b.

While certain example embodiments disclosed herein describe the prior authorization logic module 110 as being a special purpose computer separate from the service provider computer 104, in alternate embodiments, the prior authorization logic module 110 or the functions that it completes may be part of the special purpose service provider computer 104. In those embodiments where the prior authorization logic module 110 is incorporated into the service provider computer 104, and with regard to the methods described above, the elements describing transmitting or receiving between the service provider computer 104 and the prior authorization logic module 110 may be internal transmissions within the special purpose service provider computer 104 or may be omitted altogether.

Accordingly, example embodiments disclosed herein can provide the technical effects of creating a special purpose service provider computer system and method that provides a real-time or near real time way to evaluate and modify electronic prior authorization requests and responses to increase the likelihood of receiving approval of the prior authorization request earlier in the process and with fewer retransmissions of the electronic prior authorization request to the claims processor computer or prior authorization clearinghouse, thereby reducing the number of electronic prior authorization requests needing to be submitted on the network, increasing network bandwidth and improving the operations and speed of the network for the requests that are still transmitted thereon, as part of or in-line with the processing of one or more types of electronic prior authorization requests. In this regard, prescribers may more easily and more quickly obtain prior authorization approval to prescribe the medication/product/service to the patient, and thereby improving the likelihood that the patient will obtain the medication prescribed by the prescriber to the patient and follow the prescription regimen, resulting in improved patient health outcomes.

Although example embodiments of the disclosure have been described, one of ordinary skill in the art will recognize that numerous other modifications and alternative embodiments are within the scope of the disclosure. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A prescription prior authorization system facilitating interaction between a prescriber and a pharmacist comprising:
    at least one memory operable to store computer-executable instructions; and
    at least one processor configured to access the at least one memory and execute the computer-executable instructions to:
        electronically receive an electronic prior authorization request originating from a prescriber computer associated with a prescriber of a product to a patient, wherein the electronic prior authorization request comprises a plurality of data fields comprising at least one patient identifier identifying the patient, a product identifier identifying the product prescribed to the patient, a request type identifier identifying the electronic prior authorization request, and a prescriber identifier identifying the prescriber;
        identify the request type identifier in the electronic prior authorization request;
        determine, based at least on the request type identifier, at least one evaluation parameter for evaluating the electronic prior authorization request;
        determine, based at least on the at least one evaluation parameter, a plurality of required data fields in the electronic prior authorization request;
        evaluate each of the plurality of required data fields;
        determine, based at least on the evaluation, if at least one of the required data fields in the electronic prior authorization request does not include data;
        in an instance in which at least one of the required data fields in the electronic prior authorization request is determined to not include data based at least on the evaluation and an associated electronic healthcare record (EHR) field of the identified patient is populated: (a) add a data element to the determined at least one required data fields in the electronic prior authorization request from the associated electronic healthcare record (EHR) field of the identified patient, and (b) prompt a user of the prescription prior authorization system to review and accept the added data element;
        in an instance in which at least one of the required data fields in the electronic prior authorization request is determined to not include data based at least on the evaluation and an associated electronic healthcare record (EHR) field of the identified patient is not populated, prompt the user of the prescription prior authorization system to review and manually add data to the required data fields;
        electronically direct communication of the electronic prior authorization request to a pharmacy claims processor computer for processing;
        electronically receive, based at least in response to the electronic prior authorization request, an electronic prior authorization response from the pharmacy claims processor computer;
        determine, for at least a portion of the plurality of data fields in the electronic prior authorization request, a format for the data in the at least a portion of the plurality of data fields;
        compare the format of the data to a required format for the data in the at least the portion of the plurality of data fields;
        determine, based at least on the comparison of the format of the data to the required format for the data in the at least the portion of the plurality of data fields, if the format of the data in at least one of the data fields is different from the required format for the data in the respective data field;
        in an instance in which at least one of the format of the data for at least one of the required data fields is determined to be different from the required format for the data in the at least one required data fields of the electronic prior authorization request: (a) modify the format of the data determined to match the required format in the electronic prior authorization request, and (b) prompt the user of the prescription prior authorization system to review and accept the modified format of the data, wherein required data fields comprise data fields necessary to establish prior authorization, and wherein the format comprises at least one of a data character length or a data character type;
        identify a medication identifier in the electronic prior authorization response;
        determine, based at least on the medication identifier, a non-insurance based patient financial assistance opportunity that reduces or eliminates a patient financial responsibility for the medication identified by the medication identifier;
        retrieve a non-insurance based patient financial assistance opportunity message associated with the determined non-insurance based patient financial assistance opportunity for the medication;
        insert the non-insurance based patient financial opportunity assistance message into the electronic prior authorization response; and
        electronically direct communication of the electronic prior authorization response and the non-insurance based patient financial assistance opportunity message for receipt by the prescriber computer.

2. The prescription prior authorization system of claim 1, wherein the processor is further configured to access the at least one memory and execute the computer-executable instructions to:
    generate, based at least on the determination that at least one of the required data fields in the electronic prior authorization request does not include data, an electronic prior authorization response; and
    electronically direct communication of a denial of delivery of the electronic prior authorization request for receipt by the prescriber computer.

3. The prescription prior authorization system of claim 2, wherein the processor is further configured to access the at least one memory and execute the computer-executable instructions to:
generate a message identifying a basis for the denial of delivery of the electronic prior authorization request; and
insert the message identifying the basis for the denial into the denial of delivery of the electronic prior authorization request prior to directing communication of the denial of delivery of the electronic prior authorization request for receipt by the prescriber computer.

4. The prescription prior authorization system of claim 1, wherein the processor is further configured to access the at least one memory and execute the computer-executable instructions to:
generate, based at least on a positive determination that at least one of the format of the data in at least one of the data fields is different from the required format for the data in the respective data field, a denial of delivery of the electronic prior authorization request; and
electronically direct communication of a denial of delivery of the electronic prior authorization request for receipt by the prescriber computer.

5. The prescription prior authorization system of claim 1, wherein the electronic prior authorization request further comprises a diagnosis code and wherein the processor is further configured to access the at least one memory and execute the computer-executable instructions to:
identify the diagnosis code in the electronic prior authorization request;
compare the identified diagnosis code to a plurality of valid diagnosis codes to determine if the identified diagnosis code matches at least one of the plurality of valid diagnosis codes;
generate, based at least on a negative determination that the identified diagnosis code matches at least one of the valid diagnosis codes, a denial of delivery of the electronic prior authorization request; and
electronically direct communication of a denial of delivery of the electronic prior authorization request for receipt by the prescriber computer.

6. The prescription prior authorization system of claim 1, wherein the processor is further configured to access the at least one memory and execute the computer-executable instructions to:
identify a data element in one of the plurality of data fields in the electronic prior authorization request;
determine a first data format for the data element in the one data field;
determine, based at least on the at least one evaluation parameter, a required data format for the data element in the one data field;
compare the first data format to the required data format for the data element in the one data field;
determine, based at least on the comparison of the first data format to the required data format that the first data format does not match the required data format;
modify a format for the data element from the first data format to the required data format;
replace the data element in the first format in the one data field with the data element in the required data format; and
electronically direct communication of the electronic prior authorization request to a pharmacy claims processor computer for processing.

7. The prescription prior authorization system of claim 1, wherein the processor is further configured to access the at least one memory and execute the computer-executable instructions to:
electronically direct communication of the electronic prior authorization request to a pharmacy claims processor computer for processing;
electronically receive, based at least in response to the electronic prior authorization request, an electronic prior authorization response from the pharmacy claims processor computer;
identify a medication identifier in the electronic prior authorization response;
determine, based at least on the medication identifier, a message for inclusion in the electronic prior authorization response;
retrieve the message;
insert the message into the electronic prior authorization response; and
electronically direct communication of the electronic prior authorization response and the message for receipt by the prescriber computer.

8. The prescription prior authorization system of claim 1, wherein the processor is further configured to access the at least one memory and execute the computer-executable instructions to:
electronically direct communication of the electronic prior authorization request to a pharmacy claims processor computer for processing;
electronically receive, based at least in response to the electronic prior authorization request, an electronic prior authorization response from the pharmacy claims processor computer;
identify the at least one patient identifier in the electronic prior authorization response;
determine, based at least on the at least one patient identifier, a message for inclusion in the electronic prior authorization response;
retrieve the message;
insert the message into the electronic prior authorization response; and
electronically direct communication of the electronic prior authorization response and the message for receipt by the prescriber computer.

9. A computer-implemented method for providing prescription prior authorization between a prescriber and a pharmacist comprising:
electronically receiving, by a service provider computer comprising one or more processors, an electronic prior authorization request originating from a prescriber computer associated with a prescriber of a product to a patient, wherein the electronic prior authorization request comprises a plurality of data fields comprising at least one patient identifier identifying the patient, a product identifier identifying the product prescribed to the patient, a request type identifier identifying the electronic prior authorization request, and a prescriber identifier identifying the prescriber;
identifying, by the service provider computer, the request type identifier in the electronic prior authorization request;
determining, by the service provider computer and based at least on the request type identifier, at least one evaluation parameter for evaluating the electronic prior authorization request;

determining, by the service provider computer and based at least on the at least one evaluation parameter, a plurality of required data fields in the electronic prior authorization request;

evaluating, by the service provider computer, each of the plurality of required data fields;

determining, by the service provider computer and based at least on the evaluation, if at least one of the required data fields in the electronic prior authorization request does not include data;

in an instance in which at least one of the required data fields in the electronic prior authorization request is determined to not include data based at least on the evaluation and an associated electronic healthcare record (EHR) field of the identified patient is populated: (a) add a data element to the determined at least one required data fields in the electronic prior authorization request from the associated electronic healthcare record (EHR) field of the identified patient, and (b) prompt a user of the prescription prior authorization system to review and accept the added data element;

in an instance at least one of the required data fields in the electronic prior authorization request is determined to not include data based at least on the evaluation and an associated electronic healthcare record (EHR) field of the identified patient is not populated, prompt the user of the prescription prior authorization system to review and manually add data to the required data fields;

electronically transmitting, by the service provider computer, the electronic prior authorization request to a pharmacy claims processor computer for processing;

electronically receiving, by the service provider computer and based at least in response to the electronic prior authorization request, an electronic prior authorization response from the pharmacy claims processor computer;

determining, by the service provider computer and for at least a portion of the plurality of data fields in the electronic prior authorization request, a format for the data in the at least a portion of the plurality of data fields;

comparing the format of the data to a required format for the data in the at least the portion of the plurality of data fields;

determining, based at least on the comparison of the format of the data to the required format for the data in the at least the portion of the plurality of data fields, if the format of the data in at least one of the data fields is different from the required format for the data in the respective data field;

in an instance in which at least one of the format of the data for at least one of the data fields is determined to be different from the required format for the data in the at least one data fields of the electronic prior authorization request: (a) modify the format of the data determined to match the required format in the electronic prior authorization request, and (b) prompt the user of the prescription prior authorization system to review and accept the modified format of the data, wherein the format comprises at least one of a data character length or a data character type;

identifying, by the service provider computer, a medication identifier in the electronic prior authorization response;

determining, by the service provider computer and based at least on the medication identifier, a non-insurance based patient financial assistance opportunity that reduces or eliminates a patient financial responsibility for the medication identified by the medication identifier;

retrieving, by the service provider computer, a non-insurance based patient financial assistance message associated with the determined non-insurance based patient financial assistance opportunity for the medication;

inserting, by the service provider computer, the non-insurance based patient financial assistance message into the electronic prior authorization response; and electronically transmitting, by the service provider computer, the electronic prior authorization response and the non-insurance based patient financial assistance message for receipt by the prescriber computer.

10. The computer-implemented method of claim 9, further comprising:

generating, by the service provider computer and based at least on the determination that at least one of the required data fields in the electronic prior authorization request does not include data, a denial of delivery of the electronic prior authorization request; and electronically transmitting, by the service provider computer, the denial of delivery of the electronic prior authorization request for receipt by the prescriber computer.

11. The computer-implemented method of claim 10, further comprising:

generating, by the service provider computer, a message identifying a basis for the denial of delivery of the electronic prior authorization request; and inserting, by the service provider computer, the message identifying the basis for the denial of delivery into the denial of delivery of the electronic prior authorization request prior to directing communication of the denial of delivery of the electronic prior authorization request for receipt by the prescriber computer.

12. The computer-implemented method of claim 9, further comprising:

generating, by the service provider computer and based at least on a positive determination that at least one of the format of the data in at least one of the data fields is different from the required format for the data in the respective data field, a denial of delivery of the electronic prior authorization request; and electronically transmitting, by the service provider computer, the denial of delivery of the electronic prior authorization request for receipt by the prescriber computer.

13. The computer-implemented method of claim 9, wherein the electronic prior authorization request further comprises a diagnosis code and wherein the method further comprises:

identifying, by the service provider computer, the diagnosis code in the electronic prior authorization request;

comparing, by the service provider computer, the identified diagnosis code to a plurality of valid diagnosis codes to determine if the identified diagnosis code matches at least one of the plurality of valid diagnosis codes;

generating, by the service provider computer and based at least on a negative determination that the identified diagnosis code matches at least one of the valid diagnosis codes, a denial of delivery of the electronic prior authorization request; and electronically transmitting, by the service provider computer, the denial of delivery of the electronic prior authorization request for receipt by the prescriber computer.

14. The computer-implemented method of claim 9, further comprising:
   identifying, by the service provider computer, a data element in one of the plurality of data fields in the electronic prior authorization request;
   determining, by the service provider computer, a first data format for the data element in the one data field;
   determining, by the service provider computer and based at least on the at least one evaluation parameter, a required data format for the data element in the one data field;
   comparing, by the service provider computer, the first data format to the required data format for the data element in the one data field;
   determining, by the service provider computer and based at least on the comparison of the first data format to the required data format that the first data format does not match the required data format;
   modifying, by the service provider computer, a format for the data element from the first data format to the required data format;
   replacing, by the service provider computer, the data element in the first format in the one data field with the data element in the required data format; and
   electronically transmitting, by the service provider computer, the electronic prior authorization request to a pharmacy claims processor computer for processing.

15. The computer-implemented method of claim 9, further comprising:
   electronically transmitting, by the service provider computer, the electronic prior authorization request to a pharmacy claims processor computer for processing;
   electronically receiving, by the service provider computer and based at least in response to the electronic prior authorization request, an electronic prior authorization response from the pharmacy claims processor computer;
   identifying, by the service provider computer, a medication identifier in the electronic prior authorization response;
   determining, by the service provider computer and based at least on the medication identifier, a message for inclusion in the electronic prior authorization response;
   retrieving, by the service provider computer, the message;
   inserting, by the service provider computer, the message into the electronic prior authorization response; and
   electronically transmitting, by the service provider computer, the electronic prior authorization response and the message for receipt by the prescriber computer.

16. The computer-implemented method of claim 9, further comprising:
   electronically transmitting, by the service provider computer, the electronic prior authorization request to a pharmacy claims processor computer for processing;
   electronically receiving, by the service provider computer and based at least in response to the electronic prior authorization request, an electronic prior authorization response from the pharmacy claims processor computer;
   identifying, by the service provider computer, the at least one patient identifier in the electronic prior authorization response;
   determining, by the service provider computer and based at least on the at least one patient identifier, a message for inclusion in the electronic prior authorization response;
   retrieving, by the service provider computer, the message;
   inserting, by the service provider computer, the message into the electronic prior authorization response; and
   electronically transmitting, by the service provider computer, the electronic prior authorization response and the message for receipt by the prescriber computer.

\* \* \* \* \*